US007914797B2

(12) United States Patent
Arnon et al.

(10) Patent No.: US 7,914,797 B2
(45) Date of Patent: Mar. 29, 2011

(54) INFLUENZA VACCINE

(75) Inventors: Ruth Arnon, Rehovot (IL); Tamar Ben-Yedidia, Mazkeret Batya (IL)

(73) Assignee: Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 47 days.

(21) Appl. No.: 12/096,322

(22) PCT Filed: Dec. 6, 2006

(86) PCT No.: PCT/IL2006/001403
§ 371 (c)(1),
(2), (4) Date: Nov. 4, 2008

(87) PCT Pub. No.: WO2007/066334
PCT Pub. Date: Jun. 14, 2007

(65) Prior Publication Data
US 2009/0304730 A1    Dec. 10, 2009

Related U.S. Application Data

(60) Provisional application No. 60/742,574, filed on Dec. 6, 2005, provisional application No. 60/742,530, filed on Dec. 6, 2005.

(51) Int. Cl.
*A61K 39/145* (2006.01)
(52) U.S. Cl. .................. 424/206.1; 424/204.1; 435/5
(58) Field of Classification Search .................. None
See application file for complete search history.

(56) References Cited

U.S. PATENT DOCUMENTS

| 4,474,757 A | 10/1984 | Arnon et al. ..................... 424/88 |
| 6,130,082 A | 10/2000 | Majarian ..................... 435/252.3 |
| 2004/0223976 A1 | 11/2004 | Bianchi et al. ............. 424/186.1 |

FOREIGN PATENT DOCUMENTS

| WO | WO 93/20846 | * 10/1993 |
| WO | WO 94/26903 | 11/1994 |
| WO | WO 98/23735 | 6/1998 |
| WO | WO 99/07839 | 2/1999 |
| WO | WO 00/32228 | 6/2000 |
| WO | WO 0200885 | 3/2002 |
| WO | WO 2004/080403 A2 | 9/2004 |

OTHER PUBLICATIONS

Horimoto et al, Microbes and Infection, Apr. 9, 2004, vol. 6, pp. 579-583.*

Ada, G. L. and Jones, P.D. (1986) The immune response to influenza infection. Current Topics Microbiology and Immunology 128:1-54.
Arnon, R. et al., (2001) Peptide-based synthetic recombinant vaccines with anti-viral efficacy. Biologicals 29(3-4):237-242.
Ben-Yedidia, Tamar et al., (1999) Intranasal administration of peptide vaccine protects human/mouse radiation chimera from influenza infection. Int Immunol. 11(7):1043-51.
Gianfrani, Carmen et al., (2000) Human memory CTL response specific for influenza A virus is broad and multispecific. Hum Immunol. 61(5):438-452.
Ibrahim, George F. et al., (1985) Method for the isolation of highly purified *Salmonella flagellins*. J Clin Microbiol. 22(6):1040-4.
Lamb, Robert A. et al., (1985) Influenza virus M2 protein is an integral membrane protein expressed on the infected-cell surface. Cell 40:627-633.
Levi, Raphael and Arnon, Ruth (1996) Synthetic recombinant influenza vaccine induces efficient long-term immunity and cross-strain protection. Vaccine 14(1):85-92.
Liu, Wanli et al., (2005) Sequence comparison between the extracellular domain of M2 protein human and avian influenza A virus provides new information for bivalent influenza vaccine design. Microbes Infect. 7(2):1717-177.
Shapira, Michal et al., (1985) A synthetic vaccine against influenza with built-in adjuvanticity. Int J Immunopharmacol. 7(5):719-723.
Slepushkin, Vladimir A. et al., (1995) Protection of mice against influenza A virus challenge by vaccination with baculovirus-expressed M2 protein. Vaccine 13(15):1399-1402.
Townsend, A. R. M. and Skehel, J. J. (1984) The influenza A virus nucleoprotein gene controls the induction of both subtype specific and cross-reactive cytotoxic T cells. J Exp Med. 160(2):552-563.
Zou, Peng et al., (2005) The epitope recognized by a monoclonal antibody in influenza A virus M2 protein is immunogenic and confers immune protection. Int Immunopharmacol. 5(4):631-635.
Ben-Yedidya, Tamar et al., XP-000914823, "Efficacy Of Anti-Influenza Peptide Vaccine In Aged Mice",. Mechanisms of Ageing and Development, vol. 104(1), pp. 11-23 (1998).
International Search Report PCT/IL2006/001403, 2006.
Ze Chen et al., "Enhanced Protection Against a Lethal Influenza Virus Challenge by Immunization With Both Hemagglutinin- and Neuraminidase-Expressing DNAs", Vaccine, vol. 17, pp. 653-659 (1999).
Sung Ho Jeon et al., "Intranasal Immunization With Synthetic Recombinant Vaccine Containing Multiple Epitopes Of Influenza Virus," Vaccine, vol. 20, pp. 2772-2780 (2002).
Tamar Ben-Yedidia et al.,"Review: Towards an Epitope-Based Human Vaccine For Influenza", Human Vaccines vol. 1, No. 3, pp. 95-101 (2005).

* cited by examiner

*Primary Examiner* — Ali R. Salimi
(74) *Attorney, Agent, or Firm* — Winston & Strawn LLP

(57) ABSTRACT

The present invention relates to influenza vaccines for human and veterinary use. In particular, the present invention provides a vaccine able to effect long term and cross-strain protection by including at least two influenza virus epitopes expressed as a chimeric polypeptide wherein at least one epitope is influenza A virus matrix protein epitope and the second epitope is a haemagglutinin peptide epitope.

15 Claims, 8 Drawing Sheets

SEQUENCE LISTING

```
<160> NUMBER OF SEQ ID NOS: 162

<210> SEQ ID NO 1
<211> LENGTH: 4
<212> TYPE: PRT
<213> ORGANISM: INFLUENZA

<400> SEQUENCE: 1

Glu Val Glu Thr
1

<210> SEQ ID NO 2
<211> LENGTH: 15
<212> TYPE: PRT
<213> ORGANISM: INFLUENZA

<400> SEQUENCE: 2

Met Ser Leu Leu Thr Glu Val Glu Thr His Thr Arg Asn Gly Trp
1               5                   10                  15

<210> SEQ ID NO 3
<211> LENGTH: 9
<212> TYPE: PRT
<213> ORGANISM: INFLUENZA

<400> SEQUENCE: 3

Pro Ile Arg Asn Glu Trp Gly Cys Arg
1               5

<210> SEQ ID NO 4
<211> LENGTH: 10
<212> TYPE: PRT
<213> ORGANISM: INFLUENZA

<400> SEQUENCE: 4

Glu Thr Pro Ile Arg Asn Glu Trp Gly Cys
1               5                   10

<210> SEQ ID NO 5
<211> LENGTH: 11
<212> TYPE: PRT
<213> ORGANISM: INFLUENZA

<400> SEQUENCE: 5

Pro Ile Arg Asn Glu Trp Gly Cys Arg Cys Asn
1               5                   10

<210> SEQ ID NO 6
<211> LENGTH: 9
<212> TYPE: PRT
```

<213> ORGANISM: INFLUENZA

<400> SEQUENCE: 6

Leu Leu Thr Glu Val Glu Thr Pro Ile
1               5

<210> SEQ ID NO 7
<211> LENGTH: 9
<212> TYPE: PRT
<213> ORGANISM: INFLUENZA

<400> SEQUENCE: 7

Ser Leu Leu Thr Glu Val Glu Thr Pro
1 5

<210> SEQ ID NO 8
<211> LENGTH: 10
<212> TYPE: PRT
<213> ORGANISM: INFLUENZA

<400> SEQUENCE: 8

Ser Leu Leu Thr Glu Val Glu Thr Pro Ile
1 5 10

<210> SEQ ID NO 9
<211> LENGTH: 9
<212> TYPE: PRT
<213> ORGANISM: INFLUENZA

<400> SEQUENCE: 9

Leu Thr Glu Val Glu Thr Pro Leu Thr
1 5

<210> SEQ ID NO 10
<211> LENGTH: 15
<212> TYPE: PRT
<213> ORGANISM: INFLUENZA

<400> SEQUENCE: 10

Met Ser Leu Leu Thr Glu Val Glu Thr Pro Ile Arg Asn Glu Trp
1 5 10 15

<210> SEQ ID NO 11
<211> LENGTH: 18
<212> TYPE: PRT
<213> ORGANISM: INFLUENZA

<400> SEQUENCE: 11

Met Ser Leu Leu Thr Glu Val Glu Thr Pro Ile Arg Asn Glu Trp Gly
1 5 10 15

Cys Arg

<210> SEQ ID NO 12
<211> LENGTH: 15
<212> TYPE: PRT
<213> ORGANISM: INFLUENZA

<400> SEQUENCE: 12

Met Ser Leu Leu Thr Glu Val Glu Thr Leu Thr Lys Asn Gly Trp
1 5 10 15

<210> SEQ ID NO 13
<211> LENGTH: 15
<212> TYPE: PRT
<213> ORGANISM: INFLUENZA

```
<400> SEQUENCE: 13

Met Ser Leu Leu Thr Glu Val Glu Thr Leu Thr Arg Asn Gly Trp
1               5                   10                  15

<210> SEQ ID NO 14
<211> LENGTH: 9
<212> TYPE: PRT
<213> ORGANISM: INFLUENZA

<400> SEQUENCE: 14

Leu Thr Glu Val Glu Thr Pro Ile Arg
1               5

<210> SEQ ID NO 15
<211> LENGTH: 10
<212> TYPE: PRT
<213> ORGANISM: INFLUENZA

<400> SEQUENCE: 15

Leu Thr Glu Val Glu Thr Pro Ile Arg Asn
1               5                   10

<210> SEQ ID NO 16
<211> LENGTH: 9
<212> TYPE: PRT
<213> ORGANISM: INFLUENZA

<400> SEQUENCE: 16

Glu Val Glu Thr Pro Ile Arg Asn Glu
1               5

<210> SEQ ID NO 17
<211> LENGTH: 10
<212> TYPE: PRT
<213> ORGANISM: INFLUENZA

<400> SEQUENCE: 17

Glu Val Glu Thr Pro Ile Arg Asn Glu Trp
1               5                   10

<210> SEQ ID NO 18
<211> LENGTH: 11
<212> TYPE: PRT
<213> ORGANISM: INFLUENZA

<400> SEQUENCE: 18

Leu Thr Glu Val Glu Thr Pro Ile Arg Asn Glu
1               5                   10

<210> SEQ ID NO 19
<211> LENGTH: 15
<212> TYPE: PRT
<213> ORGANISM: INFLUENZA

<400> SEQUENCE: 19

Leu Thr Glu Val Glu Thr Pro Ile Arg Asn Glu Trp Gly Cys Arg
1               5                   10                  15

<210> SEQ ID NO 20
<211> LENGTH: 8
<212> TYPE: PRT
<213> ORGANISM: INFLUENZA

<400> SEQUENCE: 20
```

```
Glu Val Glu Thr Pro Ile Arg Asn
1               5

<210> SEQ ID NO 21
<211> LENGTH: 18
<212> TYPE: PRT
<213> ORGANISM: INFLUENZA

<400> SEQUENCE: 21

Met Ser Leu Leu Thr Glu Val Glu Thr Pro Thr Arg Asn Glu Trp Glu
1               5                   10                  15

Cys Arg

<210> SEQ ID NO 22
<211> LENGTH: 23
<212> TYPE: PRT
<213> ORGANISM: INFLUENZA

<400> SEQUENCE: 22

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 23
<211> LENGTH: 23
<212> TYPE: PRT
<213> ORGANISM: INFLUENZA

<400> SEQUENCE: 23

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 24
<211> LENGTH: 9
<212> TYPE: PRT
<213> ORGANISM: INFLUENZA

<400> SEQUENCE: 24

Val Glu Thr Pro Ile Arg Asn Glu Trp
1               5

<210> SEQ ID NO 25
<211> LENGTH: 11
<212> TYPE: PRT
<213> ORGANISM: INFLUENZA

<400> SEQUENCE: 25

Ser Leu Leu Thr Glu Val Glu Thr Tyr Val Leu
1               5                   10

<210> SEQ ID NO 26
<211> LENGTH: 11
<212> TYPE: PRT
<213> ORGANISM: INFLUENZA

<400> SEQUENCE: 26

Ser Leu Leu Thr Glu Val Glu Thr Tyr Val Pro
1               5                   10

<210> SEQ ID NO 27
<211> LENGTH: 9
```

```
<212> TYPE: PRT
<213> ORGANISM: INFLUENZA

<400> SEQUENCE: 27

Leu Leu Thr Glu Val Glu Thr Tyr Val
1               5

<210> SEQ ID NO 28
<211> LENGTH: 8
<212> TYPE: PRT
<213> ORGANISM: INFLUENZA

<400> SEQUENCE: 28

Ser Ile Val Pro Ser Gly Pro Leu
1               5

<210> SEQ ID NO 29
<211> LENGTH: 15
<212> TYPE: PRT
<213> ORGANISM: INFLUENZA

<400> SEQUENCE: 29

Ser Gly Pro Leu Lys Ala Glu Ile Ala Gln Arg Leu Glu Asp Val
1               5                   10                  15

<210> SEQ ID NO 30
<211> LENGTH: 12
<212> TYPE: PRT
<213> ORGANISM: INFLUENZA

<400> SEQUENCE: 30

Gly Pro Leu Lys Ala Glu Ile Ala Gln Arg Leu Glu
1               5                   10

<210> SEQ ID NO 31
<211> LENGTH: 9
<212> TYPE: PRT
<213> ORGANISM: INFLUENZA

<400> SEQUENCE: 31

Arg Leu Glu Asp Val Phe Ala Gly Lys
1               5

<210> SEQ ID NO 32
<211> LENGTH: 11
<212> TYPE: PRT
<213> ORGANISM: INFLUENZA

<400> SEQUENCE: 32

Ala Leu Met Glu Trp Leu Lys Thr Arg Pro Ile
1               5                   10

<210> SEQ ID NO 33
<211> LENGTH: 10
<212> TYPE: PRT
<213> ORGANISM: INFLUENZA

<400> SEQUENCE: 33

Pro Ile Leu Ser Pro Leu Thr Lys Gly Ile
1               5                   10

<210> SEQ ID NO 34
<211> LENGTH: 9
<212> TYPE: PRT
<213> ORGANISM: INFLUENZA
```

```
<400> SEQUENCE: 34

Ile Leu Ser Pro Leu Thr Lys Gly Ile
1               5

<210> SEQ ID NO 35
<211> LENGTH: 19
<212> TYPE: PRT
<213> ORGANISM: INFLUENZA

<400> SEQUENCE: 35

Leu Thr Lys Gly Ile Leu Gly Phe Val Phe Thr Leu Thr Val Pro Ser
1               5                   10                  15

Glu Arg Gly

<210> SEQ ID NO 36
<211> LENGTH: 13
<212> TYPE: PRT
<213> ORGANISM: INFLUENZA

<400> SEQUENCE: 36

Thr Lys Gly Ile Leu Gly Phe Val Phe Thr Leu Thr Val
1               5                   10

<210> SEQ ID NO 37
<211> LENGTH: 12
<212> TYPE: PRT
<213> ORGANISM: INFLUENZA

<400> SEQUENCE: 37

Lys Gly Ile Leu Gly Phe Val Phe Thr Leu Thr Val
1               5                   10

<210> SEQ ID NO 38
<211> LENGTH: 9
<212> TYPE: PRT
<213> ORGANISM: INFLUENZA

<400> SEQUENCE: 38

Gly Ile Leu Gly Phe Val Phe Thr Leu
1               5

<210> SEQ ID NO 39
<211> LENGTH: 9
<212> TYPE: PRT
<213> ORGANISM: INFLUENZA

<400> SEQUENCE: 39

Leu Gly Phe Val Phe Thr Leu Thr Val
1               5

<210> SEQ ID NO 40
<211> LENGTH: 9
<212> TYPE: PRT
<213> ORGANISM: INFLUENZA

<400> SEQUENCE: 40

Ile Leu Gly Phe Val Phe Thr Leu Thr
1               5

<210> SEQ ID NO 41
<211> LENGTH: 8
<212> TYPE: PRT
<213> ORGANISM: INFLUENZA

<400> SEQUENCE: 41
```

```
Ala Ser Cys Met Gly Leu Ile Tyr
1               5

<210> SEQ ID NO 42
<211> LENGTH: 9
<212> TYPE: PRT
<213> ORGANISM: INFLUENZA

<400> SEQUENCE: 42

Arg Met Gly Ala Val Thr Thr Glu Val
1               5

<210> SEQ ID NO 43
<211> LENGTH: 11
<212> TYPE: PRT
<213> ORGANISM: INFLUENZA

<400> SEQUENCE: 43

Gly Leu Val Cys Ala Thr Cys Glu Gln Ile Ala
1               5                   10

<210> SEQ ID NO 44
<211> LENGTH: 9
<212> TYPE: PRT
<213> ORGANISM: INFLUENZA

<400> SEQUENCE: 44

Gln Met Val Ala Thr Thr Asn Pro Leu
1               5

<210> SEQ ID NO 45
<211> LENGTH: 10
<212> TYPE: PRT
<213> ORGANISM: INFLUENZA

<400> SEQUENCE: 45

Gln Met Val Ala Thr Thr Asn Pro Leu Ile
1               5                   10

<210> SEQ ID NO 46
<211> LENGTH: 10
<212> TYPE: PRT
<213> ORGANISM: INFLUENZA

<400> SEQUENCE: 46

Arg Met Val Leu Ala Ser Thr Thr Ala Lys
1               5                   10

<210> SEQ ID NO 47
<211> LENGTH: 9
<212> TYPE: PRT
<213> ORGANISM: INFLUENZA

<400> SEQUENCE: 47

Asp Leu Leu Glu Asn Leu Gln Thr Tyr
1               5

<210> SEQ ID NO 48
<211> LENGTH: 18
<212> TYPE: PRT
<213> ORGANISM: INFLUENZA

<400> SEQUENCE: 48

Ser Lys Ala Tyr Ser Asn Cys Tyr Pro Tyr Asp Val Pro Asp Tyr Ala
1               5                   10                  15
```

Ser Leu

<210> SEQ ID NO 49
<211> LENGTH: 18
<212> TYPE: PRT
<213> ORGANISM: INFLUENZA

<400> SEQUENCE: 49

Ser Lys Ala Phe Ser Asn Cys Tyr Pro Tyr Asp Val Pro Asp Tyr Ala
1               5                   10                  15

Ser Leu

<210> SEQ ID NO 50
<211> LENGTH: 18
<212> TYPE: PRT
<213> ORGANISM: INFLUENZA

<400> SEQUENCE: 50

Ser Thr Ala Tyr Ser Asn Cys Tyr Pro Tyr Asp Val Pro Asp Tyr Ala
1               5                   10                  15

Ser Leu

<210> SEQ ID NO 51
<211> LENGTH: 10
<212> TYPE: PRT
<213> ORGANISM: INFLUENZA

<400> SEQUENCE: 51

Trp Leu Thr Glu Lys Glu Gly Ser Tyr Pro
1               5                   10

<210> SEQ ID NO 52
<211> LENGTH: 19
<212> TYPE: PRT
<213> ORGANISM: INFLUENZA

<400> SEQUENCE: 52

Pro Lys Tyr Val Lys Gln Asn Thr Leu Lys Leu Ala Thr Gly Met Arg
1               5                   10                  15

Asn Val Pro

<210> SEQ ID NO 53
<211> LENGTH: 11
<212> TYPE: PRT
<213> ORGANISM: INFLUENZA

<400> SEQUENCE: 53

Gly Val Lys Leu Glu Ser Met Gly Ile Tyr Gln
1               5                   10

<210> SEQ ID NO 54
<211> LENGTH: 11
<212> TYPE: PRT
<213> ORGANISM: INFLUENZA

<400> SEQUENCE: 54

Glu Ile Ser Gly Val Lys Leu Glu Ser Met Gly
1               5                   10

<210> SEQ ID NO 55
<211> LENGTH: 10
<212> TYPE: PRT
<213> ORGANISM: INFLUENZA

<400> SEQUENCE: 55

Asn Val Lys Asn Leu Tyr Glu Lys Val Lys
1               5                   10

<210> SEQ ID NO 56
<211> LENGTH: 18
<212> TYPE: PRT
<213> ORGANISM: INFLUENZA

<400> SEQUENCE: 56

Lys Val Lys Ile Leu Pro Lys Asp Arg Trp Thr Gln His Thr Thr
1               5                   10                  15
Gly Gly

<210> SEQ ID NO 57
<211> LENGTH: 13
<212> TYPE: PRT
<213> ORGANISM: INFLUENZA

<400> SEQUENCE: 57

Pro Lys Tyr Val Lys Gln Asn Thr Leu Lys Leu Ala Thr
1               5                   10

<210> SEQ ID NO 58
<211> LENGTH: 13
<212> TYPE: PRT
<213> ORGANISM: INFLUENZA

<400> SEQUENCE: 58

Pro Lys Tyr Val Lys Gln Asn Thr Leu Lys Leu Ala Thr
1               5                   10

<210> SEQ ID NO 59
<211> LENGTH: 9
<212> TYPE: PRT
<213> ORGANISM: INFLUENZA

<400> SEQUENCE: 59

Cys Thr Glu Leu Lys Leu Ser Asp Tyr
1               5

<210> SEQ ID NO 60
<211> LENGTH: 14
<212> TYPE: PRT
<213> ORGANISM: INFLUENZA

<400> SEQUENCE: 60

His Pro Ser Ala Gly Lys Asp Pro Lys Lys Thr Gly Gly Pro
1               5                   10

<210> SEQ ID NO 61
<211> LENGTH: 13
<212> TYPE: PRT
<213> ORGANISM: INFLUENZA

<400> SEQUENCE: 61

His Pro Ser Ala Gly Lys Asp Pro Lys Lys Thr Gly Gly
1               5                   10

<210> SEQ ID NO 62
<211> LENGTH: 24
<212> TYPE: PRT
<213> ORGANISM: INFLUENZA

```
<400> SEQUENCE: 62

Phe Trp Arg Gly Glu Asn Gly Arg Lys Thr Arg Ser Ala Tyr Glu Arg
1               5                   10                  15

Met Cys Asn Ile Leu Lys Gly Lys
            20

<210> SEQ ID NO 63
<211> LENGTH: 9
<212> TYPE: PRT
<213> ORGANISM: INFLUENZA

<400> SEQUENCE: 63

Ile Leu Arg Gly Ser Val Ala His Lys
1               5

<210> SEQ ID NO 64
<211> LENGTH: 9
<212> TYPE: PRT
<213> ORGANISM: INFLUENZA

<400> SEQUENCE: 64

Lys Leu Leu Gln Asn Ser Gln Val Tyr
1               5

<210> SEQ ID NO 65
<211> LENGTH: 15
<212> TYPE: PRT
<213> ORGANISM: INFLUENZA

<400> SEQUENCE: 65

Ser Ala Ala Phe Glu Asp Leu Arg Val Leu Ser Phe Ile Arg Gly
1               5                   10                  15

<210> SEQ ID NO 66
<211> LENGTH: 16
<212> TYPE: PRT
<213> ORGANISM: INFLUENZA

<400> SEQUENCE: 66

Ser Ala Ala Phe Glu Asp Leu Arg Val Ser Ser Phe Ile Arg Gly Thr
1               5                   10                  15

<210> SEQ ID NO 67
<211> LENGTH: 16
<212> TYPE: PRT
<213> ORGANISM: INFLUENZA

<400> SEQUENCE: 67

Ser Ala Ala Phe Glu Asp Leu Arg Val Leu Ser Phe Ile Arg Gly Tyr
1               5                   10                  15

<210> SEQ ID NO 68
<211> LENGTH: 14
<212> TYPE: PRT
<213> ORGANISM: INFLUENZA

<400> SEQUENCE: 68

Glu Leu Arg Ser Arg Tyr Trp Ala Ile Arg Thr Arg Ser Gly
1               5                   10

<210> SEQ ID NO 69
<211> LENGTH: 9
<212> TYPE: PRT
<213> ORGANISM: INFLUENZA
```

-continued

```
<400> SEQUENCE: 69

Glu Leu Arg Ser Arg Tyr Trp Ala Ile
1               5

<210> SEQ ID NO 70
<211> LENGTH: 9
<212> TYPE: PRT
<213> ORGANISM: INFLUENZA

<400> SEQUENCE: 70

Ser Arg Tyr Trp Ala Ile Arg Thr Arg
1               5

<210> SEQ ID NO 71
<211> LENGTH: 10
<212> TYPE: PRT
<213> ORGANISM: INFLUENZA

<400> SEQUENCE: 71

Tyr Trp Ala Ile Arg Thr Arg Ser Gly Gly
1               5                   10

<210> SEQ ID NO 72
<211> LENGTH: 9
<212> TYPE: PRT
<213> ORGANISM: INFLUENZA

<400> SEQUENCE: 72

Ser Arg Tyr Trp Ala Ile Arg Thr Arg
1               5

<210> SEQ ID NO 73
<211> LENGTH: 9
<212> TYPE: PRT
<213> ORGANISM: INFLUENZA

<400> SEQUENCE: 73

Leu Pro Phe Asp Lys Pro Thr Ile Met
1               5

<210> SEQ ID NO 74
<211> LENGTH: 9
<212> TYPE: PRT
<213> ORGANISM: INFLUENZA

<400> SEQUENCE: 74

Val Ser Asp Gly Gly Pro Asn Leu Tyr
1               5

<210> SEQ ID NO 75
<211> LENGTH: 9
<212> TYPE: PRT
<213> ORGANISM: INFLUENZA

<400> SEQUENCE: 75

Arg Arg Ser Phe Glu Leu Lys Lys Leu
1               5

<210> SEQ ID NO 76
<211> LENGTH: 9
<212> TYPE: PRT
<213> ORGANISM: INFLUENZA

<400> SEQUENCE: 76

Arg Arg Ala Thr Ala Ile Leu Arg Lys
```

```
<210> SEQ ID NO 77
<211> LENGTH: 9
<212> TYPE: PRT
<213> ORGANISM: INFLUENZA

<400> SEQUENCE: 77

Arg Pro Ile Ile Arg Pro Ala Thr Leu
1               5

<210> SEQ ID NO 78
<211> LENGTH: 9
<212> TYPE: PRT
<213> ORGANISM: INFLUENZA

<400> SEQUENCE: 78

Ala Asp Arg Gly Leu Leu Arg Asp Ile
1               5

<210> SEQ ID NO 79
<211> LENGTH: 13
<212> TYPE: PRT
<213> ORGANISM: INFLUENZA

<400> SEQUENCE: 79

Pro Tyr Tyr Thr Gly Glu His Ala Lys Ala Ile Gly Asn
1               5                   10

<210> SEQ ID NO 80
<211> LENGTH: 19
<212> TYPE: PRT
<213> ORGANISM: INFLUENZA

<400> SEQUENCE: 80

Pro Ala Lys Leu Leu Lys Glu Arg Gly Phe Phe Gly Ala Ile Ala Gly
1               5                   10                  15

Phe Leu Glu

<210> SEQ ID NO 81
<211> LENGTH: 12
<212> TYPE: DNA
<213> ORGANISM: INFLUENZA

<400> SEQUENCE: 81
gaagtggaaa cc                                                            12

<210> SEQ ID NO 82
<211> LENGTH: 45
<212> TYPE: DNA
<213> ORGANISM: INFLUENZA

<400> SEQUENCE: 82
atgagcctgc tgaccgaagt ggaaacccac accaggaatg ggtgg                        45

<210> SEQ ID NO 83
<211> LENGTH: 27
<212> TYPE: DNA
<213> ORGANISM: INFLUENZA

<400> SEQUENCE: 83
ccgattcgta acgaatgggg ttgtcgt                                            27

<210> SEQ ID NO 84
```

```
<211> LENGTH: 33
<212> TYPE: DNA
<213> ORGANISM: INFLUENZA

<400> SEQUENCE: 84
gaaaccccga ttcgtaacga atggggttgt cgt                           33

<210> SEQ ID NO 85
<211> LENGTH: 42
<212> TYPE: DNA
<213> ORGANISM: INFLUENZA

<400> SEQUENCE: 85
gaaaccccga ttcgtaacga atggggttgt cgtggttgtc gt                 42

<210> SEQ ID NO 86
<211> LENGTH: 27
<212> TYPE: DNA
<213> ORGANISM: INFLUENZA

<400> SEQUENCE: 86
ctgctgaccg aagtggaaac cccgatt                                  27

<210> SEQ ID NO 87
<211> LENGTH: 27
<212> TYPE: DNA
<213> ORGANISM: INFLUENZA

<400> SEQUENCE: 87
agcctgctga ccgaagtgga aaccccg                                  27

<210> SEQ ID NO 88
<211> LENGTH: 30
<212> TYPE: DNA
<213> ORGANISM: INFLUENZA

<400> SEQUENCE: 88
agcctgctga ccgaagtgga aaccccgatt                               30

<210> SEQ ID NO 89
<211> LENGTH: 27
<212> TYPE: DNA
<213> ORGANISM: INFLUENZA

<400> SEQUENCE: 89
ctgaccgaag tggaaacccc gctgacc                                  27

<210> SEQ ID NO 90
<211> LENGTH: 44
<212> TYPE: DNA
<213> ORGANISM: INFLUENZA

<400> SEQUENCE: 90
tgagcctgct gaccgaagtg gaaaccccga ttcgcaacga atgg               44

<210> SEQ ID NO 91
<211> LENGTH: 54
<212> TYPE: DNA
<213> ORGANISM: INFLUENZA

<400> SEQUENCE: 91
atgagcctgc tgaccgaagt ggaaaccccg attcgcaacg aatggggctg ccgc    54

<210> SEQ ID NO 92
```

```
<211> LENGTH: 45
<212> TYPE: DNA
<213> ORGANISM: INFLUENZA

<400> SEQUENCE: 92
atgagcctgc tgaccgaagt ggaaaccctg accaaaaacg gctgg            45

<210> SEQ ID NO 93
<211> LENGTH: 45
<212> TYPE: DNA
<213> ORGANISM: INFLUENZA

<400> SEQUENCE: 93
atgagcctgc tgaccgaagt ggaaaccctg acccgcaacg gctgg            45

<210> SEQ ID NO 94
<211> LENGTH: 27
<212> TYPE: DNA
<213> ORGANISM: INFLUENZA

<400> SEQUENCE: 94
ctgaccgaag tggaaacccc gattcgc                                27

<210> SEQ ID NO 95
<211> LENGTH: 30
<212> TYPE: DNA
<213> ORGANISM: INFLUENZA

<400> SEQUENCE: 95
ctgaccgaag tggaaacccc gattcgcaac                             30

<210> SEQ ID NO 96
<211> LENGTH: 27
<212> TYPE: DNA
<213> ORGANISM: INFLUENZA

<400> SEQUENCE: 96
gaagtggaaa ccccgattcg caacgaa                                27

<210> SEQ ID NO 97
<211> LENGTH: 30
<212> TYPE: DNA
<213> ORGANISM: INFLUENZA

<400> SEQUENCE: 97
gaagtggaaa ccccgattcg caacgaatgg                             30

<210> SEQ ID NO 98
<211> LENGTH: 33
<212> TYPE: DNA
<213> ORGANISM: INFLUENZA

<400> SEQUENCE: 98
ctgaccgaag tggaaacccc gattcgcaac gaa                         33

<210> SEQ ID NO 99
<211> LENGTH: 45
<212> TYPE: DNA
<213> ORGANISM: INFLUENZA

<400> SEQUENCE: 99
ctgaccgaag tggaaacccc gattcgcaac gaatgggget gccgc            45

<210> SEQ ID NO 100
```

```
<211> LENGTH: 24
<212> TYPE: DNA
<213> ORGANISM: INFLUENZA

<400> SEQUENCE: 100
gaagtggaaa ccccgattcg taac                                          24

<210> SEQ ID NO 101
<211> LENGTH: 54
<212> TYPE: DNA
<213> ORGANISM: INFLUENZA

<400> SEQUENCE: 101
atgagcctgc tgaccgaagt ggaaaccccg acccgcaacg aatgggaatg ccgc         54

<210> SEQ ID NO 102
<211> LENGTH: 69
<212> TYPE: DNA
<213> ORGANISM: INFLUENZA

<400> SEQUENCE: 102
agcctgctga ccgaagtgga accccgacc cgcaacgaat gggaatgccg ctgcagcgat    60
agcagcgat                                                           69

<210> SEQ ID NO 103
<211> LENGTH: 69
<212> TYPE: DNA
<213> ORGANISM: INFLUENZA

<400> SEQUENCE: 103
agcctgctga ccgaagtgga aacccgatt cgcaacgaat ggggctgccg ctgcaacgat    60
agcagcgat                                                           69

<210> SEQ ID NO 104
<211> LENGTH: 27
<212> TYPE: DNA
<213> ORGANISM: INFLUENZA

<400> SEQUENCE: 104
gtggaaaccc cgattcgtaa cgaatgg                                       27

<210> SEQ ID NO 105
<211> LENGTH: 33
<212> TYPE: DNA
<213> ORGANISM: INFLUENZA

<400> SEQUENCE: 105
agcctgctga ccgaagtgga aacctatgtg ctt                                33

<210> SEQ ID NO 106
<211> LENGTH: 33
<212> TYPE: DNA
<213> ORGANISM: INFLUENZA

<400> SEQUENCE: 106
agcctgctga ccgaagtgga aacctatgtg ccg                                33

<210> SEQ ID NO 107
<211> LENGTH: 27
<212> TYPE: DNA
<213> ORGANISM: INFLUENZA

<400> SEQUENCE: 107
```

-continued ctgctgaccg aagtggaaac ctatgtg                                    27

<210> SEQ ID NO 108
<211> LENGTH: 24
<212> TYPE: DNA
<213> ORGANISM: INFLUENZA

<400> SEQUENCE: 108
agcattgtgc cgagcggccc gctg                                       24

<210> SEQ ID NO 109
<211> LENGTH: 45
<212> TYPE: DNA
<213> ORGANISM: INFLUENZA

<400> SEQUENCE: 109
agcggcccgc tgaaagcgga aattgcgcag cgcctggaag atgtg                45

<210> SEQ ID NO 110
<211> LENGTH: 36
<212> TYPE: DNA
<213> ORGANISM: INFLUENZA

<400> SEQUENCE: 110
ggcccgctga agcggaaat tgcgcagcgc ctggaa                           36

<210> SEQ ID NO 111
<211> LENGTH: 27
<212> TYPE: DNA
<213> ORGANISM: INFLUENZA

<400> SEQUENCE: 111
cgcctggaag atgtgtttgc gggcaaa                                    27

<210> SEQ ID NO 112
<211> LENGTH: 30
<212> TYPE: DNA
<213> ORGANISM: INFLUENZA

<400> SEQUENCE: 112
gcgctgatgg aatggctgaa aacccgcccg                                 30

<210> SEQ ID NO 113
<211> LENGTH: 30
<212> TYPE: DNA
<213> ORGANISM: INFLUENZA

<400> SEQUENCE: 113
ccgattctga gcccgctgac caaaggcatt                                 30

<210> SEQ ID NO 114
<211> LENGTH: 27
<212> TYPE: DNA
<213> ORGANISM: INFLUENZA

<400> SEQUENCE: 114
attctgagcc cgctgaccaa aggcatt                                    27

<210> SEQ ID NO 115
<211> LENGTH: 57
<212> TYPE: DNA
<213> ORGANISM: INFLUENZA

<400> SEQUENCE: 115
ctgaccaaag gcattctggg ctttgtgttt accctgaccg tgccgagcga acgcggc    57

<210> SEQ ID NO 116
<211> LENGTH: 39
<212> TYPE: DNA
<213> ORGANISM: INFLUENZA

<400> SEQUENCE: 116
accaaaggca ttctgggctt tgtgtttacc ctgaccgtg    39

<210> SEQ ID NO 117
<211> LENGTH: 36
<212> TYPE: DNA
<213> ORGANISM: INFLUENZA

<400> SEQUENCE: 117
aaaggcattc tgggctttgt gtttaccctg accgtg    36

<210> SEQ ID NO 118
<211> LENGTH: 27
<212> TYPE: DNA
<213> ORGANISM: INFLUENZA

<400> SEQUENCE: 118
ggcattctgg gctttgtgtt taccctg    27

<210> SEQ ID NO 119
<211> LENGTH: 27
<212> TYPE: DNA
<213> ORGANISM: INFLUENZA

<400> SEQUENCE: 119
ctgggctttg tgtttaccct gaccgtg    27

<210> SEQ ID NO 120
<211> LENGTH: 27
<212> TYPE: DNA
<213> ORGANISM: INFLUENZA

<400> SEQUENCE: 120
attctgggct ttgtgtttac cctgacc    27

<210> SEQ ID NO 121
<211> LENGTH: 24
<212> TYPE: DNA
<213> ORGANISM: INFLUENZA

<400> SEQUENCE: 121
gcgagctgca tgggcctgat ttat    24

<210> SEQ ID NO 122
<211> LENGTH: 27
<212> TYPE: DNA
<213> ORGANISM: INFLUENZA

<400> SEQUENCE: 122
cgcatgggcg cggtgaccac cgaagtg    27

<210> SEQ ID NO 123
<211> LENGTH: 33
<212> TYPE: DNA
<213> ORGANISM: INFLUENZA

<400> SEQUENCE: 123

```
ggcctggtgt gcgcgacctg cgaacagatt gcg                           33
```

<210> SEQ ID NO 124
<211> LENGTH: 27
<212> TYPE: DNA
<213> ORGANISM: INFLUENZA

<400> SEQUENCE: 124

```
cagatggtgg cgaccaccaa cccgctg                                  27
```

<210> SEQ ID NO 125
<211> LENGTH: 30
<212> TYPE: DNA
<213> ORGANISM: INFLUENZA

<400> SEQUENCE: 125

```
cagatggtgg cgaccaccaa cccgctgatt                               30
```

<210> SEQ ID NO 126
<211> LENGTH: 30
<212> TYPE: DNA
<213> ORGANISM: INFLUENZA

<400> SEQUENCE: 126

```
cgcatggtgc tggcgagcac caccgcgaaa                               30
```

<210> SEQ ID NO 127
<211> LENGTH: 27
<212> TYPE: DNA
<213> ORGANISM: INFLUENZA

<400> SEQUENCE: 127

```
gatctgctgg aaaacctgca gacctat                                  27
```

<210> SEQ ID NO 128
<211> LENGTH: 54
<212> TYPE: DNA
<213> ORGANISM: INFLUENZA

<400> SEQUENCE: 128

```
agcaaagctt acagcaactg ttacccttat gatgtgccgg attatgcctc cctt    54
```

<210> SEQ ID NO 129
<211> LENGTH: 54
<212> TYPE: DNA
<213> ORGANISM: INFLUENZA

<400> SEQUENCE: 129

```
agcaaagcgt ttagcaactg ctatccgtat gatgtgccgg attatgcgag cctg    54
```

<210> SEQ ID NO 130
<211> LENGTH: 54
<212> TYPE: DNA
<213> ORGANISM: INFLUENZA

<400> SEQUENCE: 130

```
agcaccgcgt atagcaactg ctatccgtat gatgtgccgg attatgcgag cctg    54
```

<210> SEQ ID NO 131
<211> LENGTH: 30
<212> TYPE: DNA
<213> ORGANISM: INFLUENZA

<400> SEQUENCE: 131

-continued

```
tggctgacgg agaaggaggg ctcataccca                                    30

<210> SEQ ID NO 132
<211> LENGTH: 75
<212> TYPE: DNA
<213> ORGANISM: INFLUENZA

<400> SEQUENCE: 132
cccaagtatg ttaagcaaaa cactctgaag ttggcaacag ggatgcggaa tgtaccagag   60
aaacaaacta gaggc                                                   75

<210> SEQ ID NO 133
<211> LENGTH: 33
<212> TYPE: DNA
<213> ORGANISM: INFLUENZA

<400> SEQUENCE: 133
ggcgtgaaac tggaaagcat gggcatttat cag                                33

<210> SEQ ID NO 134
<211> LENGTH: 33
<212> TYPE: DNA
<213> ORGANISM: INFLUENZA

<400> SEQUENCE: 134
gaaatttccg gcgtgaaact ggaaagcatg ggc                                33

<210> SEQ ID NO 135
<211> LENGTH: 30
<212> TYPE: DNA
<213> ORGANISM: INFLUENZA

<400> SEQUENCE: 135
aacgtgaaaa acctgtatga aaaagtgaaa                                    30

<210> SEQ ID NO 136
<211> LENGTH: 54
<212> TYPE: DNA
<213> ORGANISM: INFLUENZA

<400> SEQUENCE: 136
aaagtgaaaa ttctgccgaa agatcgctgg acccagcata ccaccaccgg cggc         54

<210> SEQ ID NO 137
<211> LENGTH: 39
<212> TYPE: DNA
<213> ORGANISM: INFLUENZA

<400> SEQUENCE: 137
ccgaaatatg tgaaacagaa caccctgaaa ctggcgacc                          39

<210> SEQ ID NO 138
<211> LENGTH: 39
<212> TYPE: DNA
<213> ORGANISM: INFLUENZA

<400> SEQUENCE: 138
ccgaaatatg tgaaacagaa caccctgaaa ctggcgacc                          39

<210> SEQ ID NO 139
<211> LENGTH: 27
<212> TYPE: DNA
<213> ORGANISM: INFLUENZA
```

-continued

```
<400> SEQUENCE: 139
tgcaccgaac tgaaactgag cgattat                                          27

<210> SEQ ID NO 140
<211> LENGTH: 42
<212> TYPE: DNA
<213> ORGANISM: INFLUENZA

<400> SEQUENCE: 140
catccgagcg cgggcaaaga tccgaaaaaa accggcggcc cg                         42

<210> SEQ ID NO 141
<211> LENGTH: 39
<212> TYPE: DNA
<213> ORGANISM: INFLUENZA

<400> SEQUENCE: 141
catccgagcg cgggcaaaga tccgaaaaaa accggcggc                             39

<210> SEQ ID NO 142
<211> LENGTH: 72
<212> TYPE: DNA
<213> ORGANISM: INFLUENZA

<400> SEQUENCE: 142
ttttggcgcg gcgaaaacgg ccgcaaaacc cgcagcgcgt atgaacgcat gtgcaacatt      60
ctgaaaggca aa                                                          72

<210> SEQ ID NO 143
<211> LENGTH: 27
<212> TYPE: DNA
<213> ORGANISM: INFLUENZA

<400> SEQUENCE: 143
attctgcgcg gcagcgtggc gcataaa                                          27

<210> SEQ ID NO 144
<211> LENGTH: 27
<212> TYPE: DNA
<213> ORGANISM: INFLUENZA

<400> SEQUENCE: 144
aaactgctgc agaacagcca ggtgtat                                          27

<210> SEQ ID NO 145
<211> LENGTH: 45
<212> TYPE: DNA
<213> ORGANISM: INFLUENZA

<400> SEQUENCE: 145
agcgcggcgt ttgaagatct gcgcgtgctg agctttattc gcggc                      45

<210> SEQ ID NO 146
<211> LENGTH: 48
<212> TYPE: DNA
<213> ORGANISM: INFLUENZA

<400> SEQUENCE: 146
agcgcggcgt ttgaagatct gcgcgtgagc agctttattc gcggcacc                   48

<210> SEQ ID NO 147
<211> LENGTH: 48
<212> TYPE: DNA
```

<213> ORGANISM: INFLUENZA

<400> SEQUENCE: 147
agcgcggcgt tgaagatct gcgcgtgctg agctttattc gcggctat           48

<210> SEQ ID NO 148
<211> LENGTH: 42
<212> TYPE: DNA
<213> ORGANISM: INFLUENZA

<400> SEQUENCE: 148
gaactgcgca gccgctattg ggcgattcgc acccgcagcg gc               42

<210> SEQ ID NO 149
<211> LENGTH: 27
<212> TYPE: DNA
<213> ORGANISM: INFLUENZA

<400> SEQUENCE: 149
gaactgcgca gccgctattg ggcgatt                               27

<210> SEQ ID NO 150
<211> LENGTH: 27
<212> TYPE: DNA
<213> ORGANISM: INFLUENZA

<400> SEQUENCE: 150
agccgctatt gggcgattcg cacccgc                               27

<210> SEQ ID NO 151
<211> LENGTH: 30
<212> TYPE: DNA
<213> ORGANISM: INFLUENZA

<400> SEQUENCE: 151
tattgggcga ttcgcacccg cagcggcggc                            30

<210> SEQ ID NO 152
<211> LENGTH: 27
<212> TYPE: DNA
<213> ORGANISM: INFLUENZA

<400> SEQUENCE: 152
agccgctatt gggcgattcg cacccgc                               27

<210> SEQ ID NO 153
<211> LENGTH: 27
<212> TYPE: DNA
<213> ORGANISM: INFLUENZA

<400> SEQUENCE: 153
ctgccgtttg ataaaccgac cattatg                               27

<210> SEQ ID NO 154
<211> LENGTH: 27
<212> TYPE: DNA
<213> ORGANISM: INFLUENZA

<400> SEQUENCE: 154
gtgagcgatg gcggcccgaa cctgtat                               27

<210> SEQ ID NO 155
<211> LENGTH: 27
<212> TYPE: DNA

-continued

<213> ORGANISM: INFLUENZA

<400> SEQUENCE: 155
cgccgcagct ttgaactgaa aaaactg                                27

<210> SEQ ID NO 156
<211> LENGTH: 27
<212> TYPE: DNA
<213> ORGANISM: INFLUENZA

<400> SEQUENCE: 156
cgccgcgcga ccgcgattct gcgcaaa                                27

<210> SEQ ID NO 157
<211> LENGTH: 27
<212> TYPE: DNA
<213> ORGANISM: INFLUENZA

<400> SEQUENCE: 157
cgcccgatta ttcgcccggc gaccctg                                27

<210> SEQ ID NO 158
<211> LENGTH: 27
<212> TYPE: DNA
<213> ORGANISM: INFLUENZA

<400> SEQUENCE: 158
gcagatagag ggctattgag agacatc                                27

<210> SEQ ID NO 159
<211> LENGTH: 39
<212> TYPE: DNA
<213> ORGANISM: INFLUENZA

<400> SEQUENCE: 159
ccgtattata ccggcgaaca tgcgaaagcg attggcaac                   39

<210> SEQ ID NO 160
<211> LENGTH: 57
<212> TYPE: DNA
<213> ORGANISM: INFLUENZA

<400> SEQUENCE: 160
ccggcgaaac tgctgaaaga acgcggcttt tttggcgcga ttgcgggctt tctggaa     57

<210> SEQ ID NO 161
<211> LENGTH: 509
<212> TYPE: PRT
<213> ORGANISM: Salmonella muenchen

<400> SEQUENCE: 161

Lys Glu Lys Ile Met Ala Gln Val Ile Asn Thr Asn Ser Leu Ser Leu
1               5                   10                  15

Leu Thr Gln Asn Asn Leu Asn Lys Ser Gln Ser Ala Leu Gly Thr Ala
            20                  25                  30

Ile Glu Arg Leu Ser Ser Gly Leu Arg Ile Asn Ser Ala Lys Asp Asp
        35                  40                  45

Ala Ala Gly Gln Ala Ile Ala Asn Arg Phe Thr Ala Asn Ile Lys Gly
    50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val

```
                    85                  90                  95
Arg Glu Leu Ala Val Gln Ser Ala Asn Gly Thr Asn Ser Gln Ser Asp
                100                 105                 110

Leu Asp Ser Ile Gln Ala Glu Ile Thr Gln Arg Leu Asn Glu Ile Asp
                115                 120                 125

Arg Val Ser Gly Gln Thr Gln Phe Asn Gly Val Lys Val Leu Ala Gln
                130                 135                 140

Asp Asn Thr Leu Thr Ile Gln Val Gly Ala Asn Asp Gly Glu Thr Ile
145                 150                 155                 160

Asp Ile Asp Leu Lys Glu Ile Ser Ser Lys Thr Leu Gly Leu Asp Lys
                165                 170                 175

Leu Asn Val Gln Asp Ala Tyr Thr Pro Lys Glu Thr Ala Val Thr Val
                180                 185                 190

Asp Lys Thr Thr Tyr Lys Asn Gly Thr Asp Thr Ile Thr Ala Gln Ser
                195                 200                 205

Asn Thr Asp Ile Gln Thr Ala Ile Gly Gly Ala Thr Gly Val Thr
                210                 215                 220

Gly Ala Asp Ile Lys Phe Lys Asp Gly Gln Tyr Tyr Leu Asp Val Lys
225                 230                 235                 240

Gly Gly Ala Ser Ala Gly Val Tyr Lys Ala Thr Tyr Asp Glu Thr Thr
                245                 250                 255

Lys Lys Val Asn Ile Asp Thr Thr Asp Lys Thr Pro Leu Ala Thr Ala
                260                 265                 270

Glu Ala Thr Ala Ile Arg Gly Thr Ala Thr Ile Thr His Asn Gln Ile
                275                 280                 285

Ala Glu Val Thr Lys Glu Gly Val Asp Thr Thr Thr Val Ala Ala Gln
                290                 295                 300

Leu Ala Ala Ala Gly Val Thr Gly Ala Asp Lys Asp Asn Thr Ser Leu
305                 310                 315                 320

Val Lys Leu Ser Phe Glu Asp Lys Asn Gly Lys Val Ile Asp Gly Gly
                325                 330                 335

Tyr Ala Val Lys Met Gly Asp Asp Phe Tyr Ala Ala Thr Tyr Asp Glu
                340                 345                 350

Lys Gln Val Gln Leu Leu Asn Asn His Tyr Thr Asp Gly Ala Gly
                355                 360                 365

Val Leu Gln Thr Gly Ala Val Lys Phe Gly Gly Ala Asn Gly Lys Ser
                370                 375                 380

Glu Val Val Thr Ala Thr Val Gly Lys Thr Tyr Leu Ala Ser Asp Leu
385                 390                 395                 400

Asp Lys His Asn Phe Arg Thr Gly Gly Glu Leu Lys Glu Val Asn Thr
                405                 410                 415

Asp Lys Thr Glu Asn Pro Leu Gln Lys Ile Asp Ala Ala Leu Ala Gln
                420                 425                 430

Val Asp Thr Leu Arg Ser Asp Leu Gly Ala Val Gln Asn Arg Phe Asn
                435                 440                 445

Ser Ala Ile Thr Asn Leu Gly Asn Thr Val Asn Asn Leu Ser Ser Ala
450                 455                 460

Arg Ser Arg Ile Glu Asp Ser Asp Tyr Ala Thr Glu Val Ser Asn Met
465                 470                 475                 480

Ser Arg Ala Gln Ile Leu Gln Gln Ala Gly Thr Ser Val Leu Ala Gln
                485                 490                 495

Ala Asn Gln Val Pro Gln Asn Val Leu Ser Leu Leu Arg
                500                 505
```

```
<210> SEQ ID NO 162
<211> LENGTH: 1530
<212> TYPE: DNA
<213> ORGANISM: Salmonella muenchen

<400> SEQUENCE: 162
aaggaaaaga tcatggcaca agtcattaat acaaacagcc tgtcgctgtt gacccagaat      60
aacctgaaca atcccagtc cgctctgggc accgctatcg agcgtctgtc ttccggtctg      120
cgtatcaaca gcgcgaaaga cgatgcggca ggtcaggcga ttgctaaccg tttcaccgcg      180
aacatcaaag gtctgactca ggcttcccgt aacgctaacg acggtatctc cattgcgcag      240
accactgaag gcgcgctgaa cgaaatcaac aacaacctgc agcgtgtgcg tgaactggcg      300
gttcagtctg ctaacggtac taactcccag tctgaccttg actctatcca ggctgaaatc      360
acccagcgtc tgaacgaaat cgaccgtgta tccggtcaga ctcagttcaa cggcgtgaaa      420
gtcctggcgc aggacaacac cctgaccatc caggttggtg ccaacgacgg tgaaactatt      480
gatattgatt taaaagaaat tagctctaaa acactgggac ttgataagct taatgtccag      540
gatgcctaca ccccgaaaga aactgctgta accgttgata aaactaccta taaaaatggt      600
acagatacta ttacagccca gagcaatact gatatccaaa ctgcaattgg cggtggtgca      660
acggggggtta ctggggctga tatcaaattt aaagatggtc aatactattt agatgttaaa      720
ggcggtgctt ctgctggtgt ttataaagcc acttatgatg aaactacaaa gaaagttaat      780
attgatacga ctgataaaac tccgttagca actgcggaag ctacagctat tcggggaacg      840
gccactataa cccacaacca aattgctgaa gtaacaaaag agggtgttga tacgaccaca      900
gttgcggctc aacttgctgc tgcaggggtt actggtgccg ataaggacaa tactagcctt      960
gtaaaactat cgtttgagga taaaaacggt aaggttattg atggtggcta tgcagtgaaa     1020
atgggcgacg atttctatgc cgctacatat gatgagaaac aggtacaatt actgctaaac     1080
aaccactata cagatggtgc tggcgtgctc caaactggag ctgtgaaatt tggtggcgca     1140
aatggtaaat ctgaagttgt tactgctacc gtaggtaaaa cttacttagc aagcgaccTt     1200
gacaaacata acttcagaac aggcggtgag cttaaagagg ttaatacaga taagactgaa     1260
aacccactgc agaaaattga tgctgccttg gcacaggttg atacacttcg ttctgacctg     1320
ggtgcggtac agaaccgttt caactccgct atcaccaacc tgggcaatac cgtaaataac     1380
ctgtcttctg cccgtagccg tatcgaagat tccgactacg cgaccgaagt ctccaacatg     1440
tctcgcgcgc agattctgca gcaggccggt acctccgttc tggcgcaggc taaccaggtt     1500
ccgcaaaacg tcctctcttt actgcgttaa                                     1530
```

US 7,914,797 B2

INFLUENZA VACCINE

This application is a 371 filing of International Patent Application PCT/IL2006/001403 filed Dec. 6, 2006, which claims the benefit of provisional application Nos. 60/742,574 and 60/742,530, each filed Dec. 6, 2005.

FIELD OF THE INVENTION

The present invention relates generally to influenza vaccines for human and veterinary use. In particular, the present invention provides a vaccine able to elicit long term and cross-strain protection comprising a plurality of chimeric proteins comprising at least two influenza virus peptide epitopes wherein at least one epitope is an influenza A virus matrix protein (M) peptide epitope and the second epitope is a haemagglutinin (HA) peptide epitope. Particularly advantageous epitopes include M1 or M2 N-terminus peptide epitopes and an influenza A or influenza B B-cell type HA epitope.

BACKGROUND OF THE INVENTION

Influenza

Influenza is a disease caused by viruses of three main subtypes, Influenza A, B and C, which are classified according to their antigenic determinants. The influenza virion consists of a single stranded RNA genome closely associated with a nucleoprotein (NP) and enclosed by a lipoprotein envelope lined by matrix protein (M1) and carrying two major surface glycoprotein antigens, haemagglutinin (HA) and neuraminidase (NA). The HA and NA glycoproteins are most susceptible to change; for example, there are 16 immune classes of HA and 9 different NA classes that provide the basis for the different influenza virus subtypes like H1N1 or H3N2. Influenza A virus has an additional transmembrane glycoprotein, M2, which is highly conserved between the different HN subtypes. The M2 gene encodes a protein having 96-97-amino-acids that is expressed as a tetramer on the virion cell surface. It is composed of about 24 extracellular amino acids, about 19 transmembrane amino acids, and about 54 cytoplasmic residues (Lamb et al, 1985).

Influenza A and B viruses are the most common causes of influenza in man. Influenza has an enormous impact on public health with severe economic implications in addition to the devastating health problems, including morbidity and even mortality. Infection may be mild, moderate or severe, ranging from asymptomatic through mild upper respiratory infection and tracheobronchitis to a severe, occasionally lethal, viral pneumonia.

Influenza viruses have two important immunological characteristics that present a challenge to vaccine preparation. The first concerns genetic changes that occur in the surface glycoproteins every few years, referred to as "antigenic drift". This antigenic change produces viruses that elude resistance elicited by existing vaccines. The second characteristic of great public health concern is that influenza viruses, in particular influenza A virus can exchange genetic material and merge. This process, known as "antigenic shift", results in new strains different from both parent viruses, which can be lethal pandemic strains. Avian influenza is an influenza A virus that has crossed the species barrier from birds to mammals, including humans.

Avian Influenza

Most avian influenza (AI) strains are classified as low pathogenic avian influenza (LPAI) and cause few clinical signs in infected birds. In contrast, high pathogenic avian influenza (HPAI) strains cause a severe and extremely contagious illness and death among infected birds.

Humans are not commonly affected by avian flu, however, the epidemics of highly pathogenic avian influenza (HPAI) recently seen in poultry in Asia increase opportunities for human exposure and infection. Severe cases have been reported in the past and during the current epidemics in Asia. Recent highly pathogenic outbreaks have been caused by influenza A viruses of subtypes H5 and H7. Of the 15 avian influenza virus subtypes, H5N1 is of particular concern since it mutates rapidly and has a documented propensity to acquire genes from viruses infecting other animal species. Its ability to cause disease in humans is now well documented. Birds that survive infection excrete virus for at least 10 days, orally and in feces, thus facilitating further spread at live poultry markets and by migratory birds.

The epidemic of HPAI caused by H5N1, which began in mid-December 2003 in certain Asian countries has spread and poses a public health concern. The spread of infection in birds increases the opportunities for direct infection of humans. If more humans become infected over time, the likelihood also increases that humans, if concurrently infected with human and avian influenza strains, could serve as the host for the emergence of a novel subtype with sufficient human influenza genes to be easily transmitted from person to person. Such an event would mark the start of an influenza pandemic.

AI spread between birds occurs primarily by direct contact between healthy birds and infected birds, and through indirect contact with contaminated equipment and materials. The virus is excreted through the feces of infected birds and through secretions from the nose, mouth and eyes.

Contact with infected fecal material is the most common mode of bird-to-bird transmission. Wild ducks often introduce low pathogenicity viruses into domestic flocks raised on range or in open flight pens through fecal contamination. Within a poultry house, transfer of the HPAI virus between birds can also occur via airborne secretions. The spread of avian influenza between poultry premises almost always follows the movement of contaminated people and equipment. Transfer of eggs is also a potential means of AI transmission.

Influenza Virus Antigens and Vaccine Production

Immunization towards influenza virus is limited by the antigenic variation of the virus and by the restriction of the infection to the respiratory mucous membranes. The influenza vaccines currently available are based either on whole inactive virus, or on antigenic determinants of the surface proteins. HA is a strong immunogen and is the most significant antigen in defining the serological specificity of the different virus strains.

The HA molecule (75-80 kD) comprises a plurality of antigenic determinants, several of which are in regions that undergo sequence changes in different strains (strain-specific determinants) and others in regions which are conserved in many HA molecules (common determinants). Due to these changes, flu vaccines need to be modified at least every few years.

Many influenza antigens, and vaccines prepared therefrom, are known in the art. U.S. Pat. No. 4,474,757 discloses a vaccine against influenza virus infections consisting of a synthetic peptide corresponding to an antigenic fragment of HA attached to a suitable macromolecular carrier, such as polymers of amino acids or tetanus toxoid.

PCT International Publication WO 93/20846 to some of the inventors of the present invention teaches a synthetic recombinant vaccine against a plurality of different influenza virus strains comprising at least one recombinant protein comprising the amino acid sequence of flagellin and at least one amino acid sequence of an epitope of influenza virus HA or NP, or an aggregate of said chimeric protein. Following this approach, a synthetic recombinant anti-influenza vaccine based on three epitopes was found to be highly efficient in mice. The exemplified vaccines included flagellin chimeras comprising the HA 91-108 epitope, a B-cell epitope from the HA which is conserved in all H3 strains and elicits anti-influenza neutralizing antibodies, together with one or both T-helper or CTL NP epitopes (NP 55-69 and NP 147-158, respectively), which induce MHC-restricted immune responses. A vaccine comprising a combination of the three above mentioned chimeras was considered to afford the best protection to viral infection.

PCT application publication WO 00/32228 to some of the inventors of the present invention teaches a human synthetic peptide-based influenza vaccine comprising at least four epitopes of influenza virus, said influenza virus epitopes being reactive with human cells, said epitopes comprising: (i) one B-cell haemagglutinin (HA) epitope; (ii) one T-helper haemagglutinin (HA) or nucleoprotein (NP) epitope that can bind to many HLA molecules; and (iii) at least two cytotoxic lymphocyte (CTL) nucleoprotein (NP) or matrix protein (M) epitopes that are restricted to the most prevalent HLA molecules in different human populations, in particular specific ethnic or racial groups. The influenza peptide epitopes can be expressed as recombinant *Salmonella* flagellin. That vaccine requires the cumbersome preparation of at least four chimeric polypeptides.

PCT Application Publication WO 2004/080403 and US Patent Application Publication US2004/0223976 provide a vaccine against disease caused by infection with influenza virus, and methods of vaccination. Each vaccine comprises a plurality of peptides derived from the M2 and/or HA proteins of influenza virus chemically conjugated to a carrier protein. The conjugation is between one terminus of the peptide and a reactive site of the carrier protein where the carrier protein is selected from the outer membrane protein complex of *Neisseria meningitidis*, tetanus toxoid, hepatitis B surface antigen or core antigen, keyhole limpet hemocyanin, rotavirus capsid protein, and the L1 protein of bovine or human papillomavirus VLP. That disclosure requires a plurality of M2 or HA peptide epitopes covalently bound to the outer surface of a carrier protein and neither suggests nor teaches a vaccine comprising a chimeric polypeptide.

PCT Application Publication WO 99/07839 relates to influenza antigens for use in vaccines wherein the vaccines are comprised of a fusion product of at least the extracellular part of M2 and a presenting carrier. The M2 fragment was fused to the amino terminus of the carrier protein in order to retain a free N-terminus of the M2-domain and in this way mimic the wild type structure of the M2 protein. Furthermore that invention is exemplified by way of a M2 fusion protein wherein the intact extracellular portion of M2 fragment is fused to the N-terminus of the hepatitis B virus core protein in order to mimic the wild type structure of the M2 protein in viral particles and on infected cells, where the free N-terminus extends in the extracellular environment. That application neither teaches nor suggests an isolated M2 epitope that is conformationally constrained.

International Patent Application Publication No. WO 99/07839 teaches an immunogenic extracellular portion of a M2 membrane protein of an influenza A virus fused to a presenting carrier, which can be selected from the amino terminus of the human Hepatitis B virus core protein, third complement protein fragment d (C3d), tetanus toxin fragment C or yeast Ty particles. Other non-peptidic presenting carriers are mentioned, yet that invention is exemplified only by genetic fusion products.

Slepushkin et al. (1995) describes protection of mice to influenza A challenge by vaccination with a recombinant M2 protein expressed in baculovirus and administered with Freund's adjuvant.

PCT Application Publication No. WO 98/23735 discloses an influenza vaccine for inducing a cell-mediated cytolytic immune response against an antigen in a mammal comprising a fusion product of an influenza antigen and a stress protein or heat shock protein as carrier. The influenza antigen is selected from hemagglutinin, nucleoprotein, neuraminidase, M1, M2, PB1, PB2, PA and a combination thereof. There is neither teaching nor suggestion of a vaccine combining a M epitope with a HA epitope.

Zou, et al. (2005) teach the extracellular M2 6-13 peptide and suggest that that sequence may be useful in the preparation of an influenza vaccine. Liu, et al (2005) disclose host specific epitopes within the extracellular M2 sequences, which may be useful for the preparation of a bivalent influenza vaccine. The relevant epitopes include the M2 10-20 sequence common to human, avian and swine influenza.

PCT Application Publication No. WO 94/26903 relates to human influenza matrix protein peptides able to bind to human MHC Class I molecules. That invention provides candidate peptide epitopes able to bind to the groove of MHC class I molecules. identified using the antigen processing defective cell line174.CEM T2 (T2). There is neither teaching nor suggestion of a vaccine comprising a combination of M peptide epitope with a HA peptide epitope.

It would be highly advantageous to have an influenza vaccine that could be administered once and confer protection for several years or even a lifetime by providing cross-protection against new strains of viruses.

There remains an unmet need for a vaccine useful in eliciting an immune response to a broad range of influenza subtypes that affords long term and cross-species protection, is both cost effective and readily produced, can be administered in a variety of forms and is useful for animal and human immunization.

SUMMARY OF THE INVENTION

The present invention provides an influenza vaccine eliciting long-term and cross-subtype protection against infection with influenza A and influenza B viruses, including the avian influenza serotypes. An unexpectedly robust immune response to influenza A or B virus is elicited by a vaccine comprising chimeric proteins which comprise at least one influenza A matrix protein (M) peptide epitope and at least one influenza A or B haemagglutinin (HA) peptide epitope. A vaccine comprising a combination of a M and a HA epitope overcomes drawbacks of the known vaccines including the need for including epitopes that are restricted to HLA molecules associated with different racial or ethnic populations. The vaccine of the present invention elicits cross-racial efficacy and Asian and African populations react as well as Caucasians.

Additionally, a surprisingly effective immune response to influenza A or B virus is elicited by a vaccine comprising a chimeric protein comprising a M2 peptide epitope and a flagellin amino acid sequence wherein the M2 peptide epitope is embedded within the flagellin polypeptide sequence. This finding is unexpected in view of the hitherto known M2 fusion proteins and conjugates that comprise at least the entire M2 extracellular region and mimic the conformation of the entire extracellular domain of the M2 protein.

In one aspect the present invention provides a vaccine for immunization of a subject comprising a plurality of chimeric proteins comprising at least two influenza virus peptide epitopes wherein the first peptide epitope is an influenza A virus matrix (M) peptide epitope and a second peptide epitope is a haemagglutinin (HA) peptide epitope, wherein the vaccine elicits cross strain protection.

In one embodiment the M peptide epitope is selected from a M1 or a M2 peptide epitope. In various embodiments the M peptide epitope is derived from the N-terminal domain of the M1 or M2 glycoprotein. The M glycoprotein may be derived from any one of the influenza A virus subtypes, including H3N2, H5N1 and the like.

In some embodiments the M1 peptide epitope comprises from about 5 to about 18 contiguous amino acids derived from the M1 N-terminal domain. In certain embodiments the M1 epitope comprises from about 8 to about 15 contiguous amino acids derived from a MM1 N-terminal domain. According to some embodiments the M1 epitope is selected from

| M1 2-12 | SLLTEVETYVP | (SEQ ID NO: 26) |
| M1 3-11 | LLTEVETYV | (SEQ ID NO: 27) |
| M1 13-21 | SIVPSGPL | (SEQ ID NO: 28) |
| M1 17-31 | SGPLKAEIAQRLEDV | (SEQ ID NO: 29) |
| M1 18-29 | GPLKAEIAQRLE | (SEQ ID NO: 30) |

In certain embodiments the M1 peptide epitope is selected from M1 2-12 (SEQ ID NO:26) and M1 3-11 (SEQ ID NO:27).

In some embodiments the M2 peptide epitope comprises from about 5 to about 20 contiguous amino acids derived from a M2 extracellular domain. In certain embodiments the M2 peptide epitope comprises from about 8 to about 18 contiguous amino acids derived from a M2 extracellular domain. In certain embodiments M2 peptide epitope is conserved in all H3 subtypes. In other embodiments the M2 peptide epitope is derived from a M2 extracellular domain of an H5, H7 or an H9 subtype.

In one embodiment the M2 peptide epitope comprises the M2 6-9 epitope having amino acid sequence EVET, set forth in SEQ ID NO:1. In some embodiments the M2 epitope is selected from the group consisting of M2 3-11 peptide having amino acid sequence LLTEVETPI set forth in SEQ ID NO:6;

M2 2-10 peptide having amino acid sequence SLLTEVETP, set forth in SEQ ID NO:7;

M2 2-11 peptide having amino acid sequence SLLTEVETPI, set forth in SEQ ID NO:8;

M2 1-15 peptide having amino acid sequence MSLLTEVETHTRNGW set forth in SEQ ID NO:2.

M2 1-15 peptide having amino acid sequence MSLLTEVETPIRNEW, set forth in SEQ ID NO:10;

M2 1-18 peptide having amino acid sequence MSLLTEVETPIRNEWGCR, set forth in SEQ ID NO: 11;

M2 1-15 peptide having amino acid sequence MSLLTEVETLTKNGW set forth in SEQ ID NO:12;

M2 1-15 peptide having amino acid sequence MSLLTEVETLTRKGW set forth in SEQ ID NO:13; and M2 6-13 peptide having amino acid sequence EVETPIRN, set forth in SEQ ID NO:20;

An exemplary list of M peptide epitopes useful in the vaccine of the present invention can be found in Table 1 herein below.

In various embodiments the HA epitope is an influenza A or influenza B B-cell type peptide epitope. In some embodiments the HA peptide epitope is selected from the group consisting of HA 91-108 (SEQ ID NO:48), HA 91-108 (SEQ ID NO:49), and HA 107-124 (SEQ ID NO:50). An exemplary list of HA epitopes useful in the vaccine of the present invention can be found in Table 2 herein below.

In some embodiments the HA peptide epitope is an influenza B HA peptide epitope. Exemplary influenza B HA peptide epitopes are HA 354-372 (SEQ ID NO:80) and 308-320 (SEQ ID NO:79).

According to some embodiments the vaccine of the present invention comprises the M1 2-12 (SEQ ID NO:26) and HA 91-108 (SEQ ID NO:48) influenza A peptide epitopes. In other embodiments the vaccine of the present invention comprises the M2 1-18 (SEQ ID NO:11) and HA 91-108 (SEQ ID NO:48) influenza A peptide epitopes.

Additionally, the vaccine of the present invention may further comprise additional antigenic peptides of influenza A or influenza B virus, in particular B-cell type and T helper type peptide epitopes. In various embodiments the vaccine further comprises at least one influenza A T helper (Th) type peptide epitope. The T helper type peptide epitope may be selected from a M, NP, HA or polymerase (PB) peptide epitope. Certain preferred peptide epitopes include HA 307-319 (SEQ ID NO:57), HA 128-145 (SEQ ID NO:56), HA 306-324 (SEQ ID NO:52), and NP 206-229 (SEQ ID NO:62)

In other embodiments the vaccine may further comprise one or more B-cell type peptide epitopes. Certain preferred B-cell type peptide epitopes include HA 150-159 (SEQ ID NO:51) and M2 6-13 (SEQ ID NO:20).

In various embodiments the vaccine may further comprise additional influenza A or influenza B peptide epitopes. Certain preferred peptide epitopes include one or more of a B cell, Th or CTL type peptide epitopes or a combination thereof.

In some embodiments one or more CTL type epitopes that are restricted to prevalent HLA molecules in different populations are preferred. Examples of peptide epitopes useful in the vaccine of the present invention may be found in the tables set forth hereinbelow. Certain preferred CTL type peptide epitopes include NP 335-350 (SEQ ID NO:66) or (SEQ ID NO:67), NP 380-393 (SEQ ID NO:68).

In some embodiments the peptide vaccine comprises an influenza A virus M1 peptide epitope selected from M1 2-12 (SEQ ID NO:26) and M1 3-11 (SEQ ID NO:27); a HA 91-108 (SEQ ID NOS:48) peptide epitope and a Th type peptide epitope selected from a Th HA peptide epitope and a Th NP peptide epitope.

In other embodiments the peptide vaccine comprises an influenza A virus M2 peptide epitope selected from M2 1-18 (SEQ ID NO:11) and M2 1-15; a HA 91-108 peptide epitope and a Th type peptide epitope selected from a Th HA peptide epitope and a Th NP peptide epitope.

In some embodiments the vaccine comprises M1 1-12; HA 91-108; HA 307-319 (SEQ ID NO:57): at least one CTL type NP peptide epitope selected from the group consisting of NP 335-350 (SEQ ID NO:67), NP 380-393 (SEQ ID NO:68), NP 265-273 (SEQ ID NO:63). In other embodiments the vaccine further comprises an influenza B peptide epitope. In some embodiments the influenza B epitope is HA 354-372 having amino acid sequence set forth in SEQ ID NO:80.

In one embodiment the vaccine comprises M1 1-12; HA 91-108; HA 307-319, NP 335-350, NP 380-393. In other embodiments the vaccine further comprises HA 354-372. In Other embodiments the synthetic vaccine comprises M2 1-18; HA 91-108; HA 307-319, NP 335-350, NP 380-393. In other embodiments the vaccine further comprises HA 354-372.

The peptide epitopes may be expressed as recombinant flagella, wherein each recombinant flagellin comprises one or more peptide epitopes. Alternatively, the peptide epitopes can be expressed in an expression vector as a recombinant peptide protein which can be fused to a heterologous protein. In some embodiments an adjuvant or carrier is required. Accordingly, the present invention provides a synthetic or recombinant peptide-based vaccine for immunization of a subject comprising at least two influenza virus epitopes wherein the first epitope is an influenza A virus matrix (M) peptide epitope and a second epitope is a haemagglutinin (HA) epitope; and a pharmaceutically acceptable adjuvant or carrier.

In another aspect the present invention provides a vaccine for immunization of a subject comprising a plurality of chimeric proteins comprising at least two influenza virus peptide epitopes wherein the first peptide epitope is an influenza A virus matrix (M) peptide epitope and a second peptide epitope is a haemagglutinin (HA) peptide epitope; wherein each of said epitopes is expressed individually or together as a chimeric polypeptide.

The chimeric polypeptide of the present invention does not include conjugates in which peptide epitopes are conjugates to the outer surface of a carrier.

In some embodiments the present invention provides a vaccine comprising at least two recombinant flagellin molecules wherein one recombinant flagellin comprises an influenza A virus M peptide epitope and a second recombinant flagellin comprises a HA peptide epitope.

The sequence of the flagellin is not limiting in the present invention and can be selected from known flagellin sequences In certain preferred embodiments the recombinant flagellin comprises an amino sequence set forth in SEQ ID NO:161 (accession number CAA27130) and is encoded by a polynucleotide sequence set forth in SEQ ID NO:162. In other embodiments the chimeric polypeptide comprises modified flagellin.

The vaccine of the present invention is intended for human and veterinary applications including immunization of domestic animals (dog, cat, monkey etc.); livestock (horse, cow, sheep, goat, pig etc.), wild birds (wild geese, wild ducks, etc.) and domestic birds (chicken, duck, geese etc.). Therefore, in addition to the M and HA epitopes the vaccine of the present invention may optionally further comprise Th and or CTL type peptide epitopes selected from species specific strains of influenza. The present invention further provides the use of at least one influenza A M peptide epitope and at least one HA peptide epitope for the preparation of a synthetic influenza vaccine.

In another aspect, the present invention provides a polynucleotide construct comprising a polynucleotide sequence of a nuclei acid sequence of an influenza peptide epitope according to the present invention operably linked to an expression vector. The polynucleotide construct expresses the chimeric polypeptide. The present invention further encompasses host cell comprising the polynucleotide construct.

In a third aspect the present invention provides a method for eliciting an immune response and conferring protection against influenza virus in a subject, wherein the method comprises administering to the subject a vaccine comprising a plurality of chimeric proteins comprising at least two influenza virus peptide epitopes wherein the first peptide epitope is an influenza A virus matrix (M) peptide epitope and a second peptide epitope is a haemagglutinin (HA) peptide epitope, wherein the vaccine elicits cross strain protection.

In some embodiments the vaccine protects against influenza A, including avian influenza. In other embodiments the vaccine comprises an influenza B epitope and elicits protection against influenza B. In another embodiment the vaccine comprises peptide epitopes that elicit protection to both influenza A and influenza B virus.

Routes of administration of the vaccine include, but are not limited to intraperitoneal, subcutaneous, intranasal, intramuscular, oral, topical and transdermal delivery. Preferred routes of administration include oral, intranasal (IN) and intramuscular (IM) administration. In one embodiment the vaccine is formulated for intranasal administration. In another embodiment the vaccine is formulated for intramuscular administration It is to be explicitly understood that known compositions are to be excluded from the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 presents a graph showing interferon gamma (IFNγ) secretion from lymphocytes incubated with the respective peptide after the second and third immunization of HHD/HLA A2 transgenic (TG) mice.

FIGS. 2A-2C show lysis of target cells by NK (Natural Killer cells) derived from mice immunized with individual or combination epitopes following the second (2A) and third immunization (2B). Even after the second immunization, NK cells from the mice immunized with the combination of 6 epitopes (hexa-vaccine1) were able to lyse the target cells more efficiently than the cells from mice vaccinated with the native flagella (2C). Specific lysis was determined at different E:T ratios.

FIGS. 3A and 3B show the results of immunizing C57Bl/6 mice with Hexa-vaccine2, consisting of recombinant flagella comprising the HA 91-108, HA 354-372, HA 307-319, NP 335-350, NP 380-393 and M2 1-18 peptide epitopes. Serum was tested following 3 immunizations and the specificity of antibody (Ab or Ig) against the whole H3N2 influenza virus (3A) and against the specific M2 1-18 peptide (3B) was determined.

FIG. 4 shows binding of peptide epitopes to HLA-A2 on T2 cells: High and dose dependent binding was shown by the M1 3-11 peptide. Other tested peptides, NP 336-344, NP 380-388 and HA 307-319, also showed binding capacity, which was not dose dependent.

FIGS. 5A-5C show antibody protection elicited by the recombinant peptide epitopes. A significant elevation in antibody (Ab) titer, specific to each epitope was obtained with epitopes M1 2-12, NP 335-350 and HA 91-108 in mice immunized with the single relevant epitope.

FIG. 6 shows the humoral immune dose response obtained following vaccination of mice with Hexa-vaccine1.

FIG. 7 shows the humoral immune response to flagella following intranasal and intramuscular administration of the Hexa-vaccine1.

FIG. 8 shows the results of virus titration. After three vaccinations with Hexa-vaccine1, mice were infected with a sub-lethal dose of influenza virus H3N2 strain (A/Texas/1/77). The lungs of the mice were removed 5 days later for titration of viral load. The titration was performed in fertilized eggs.

FIG. 9 presents the IgE titer in the dosing experiment and in the experiment for evaluating the cellular response.

Figure 12:
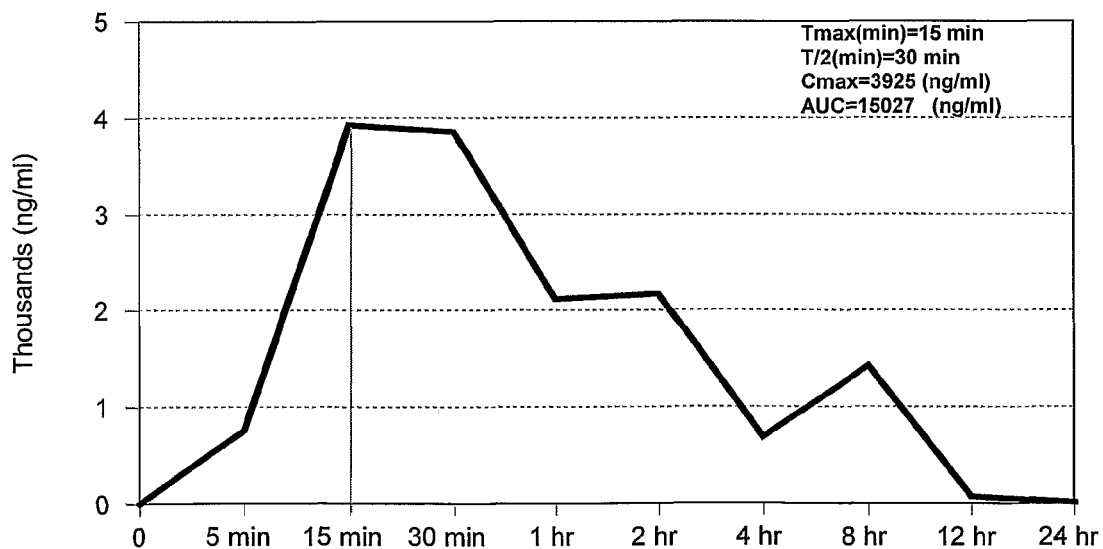

FIG. 12 depicts pharmacokinetic data. Maximum serum concentration of Hexa-vaccine1 was observed after 15 minutes ($T_{max}$). Half ($T_{1/2}$) of the total exposure quantity was obtained within 30 minutes post dosing. Protein could not be detected after 12 hours.

DETAILED DESCRIPTION OF THE INVENTION

The present invention is based on the unexpected discovery that a vaccine comprising at least one M peptide epitope and at least one HA peptide epitope is able to elicit long-term and cross strain protective immunity to influenza.

Definitions

For convenience, certain terms employed in the specification, examples and claims are described herein.

The term "antigen presentation" means the expression of antigen on the surface of a cell in association with major histocompatability complex class I or class II molecules (MHC-I or MHC-II) of animals or with the HLA-I and HLA-II of humans.

The term "immunogenicity" or "immunogenic" relates to the ability of a substance to stimulate or elicit an immune response. Immunogenicity is measured, for example, by determining the presence of antibodies specific for the substance. The presence of antibodies is detected by methods known in the art, for example using an ELISA assay.

Influenza epitopes can be classified as B-cell type, T-cell type or both B cell and T cell type, depending on the type of immune response they elicit. The definition of B cell or T cell peptide epitope is not unequivocal; for example, a peptide epitope can induce antibody production but at the same time that epitope can possess a sequence that enables binding to the human HLA molecule, rendering it accessible to CTLs, hence a dual B cell and T cell classification for that particular epitope. "CTL", "killer T cells" or "cytotoxic T cells" is a group of differentiated T cells that recognize and lyse target cells bearing a specific foreign antigen that function in defense against viral infection and cancer cells. "T helper cell" or "Th" is any of the T cells that when stimulated by a specific antigen release cytokines that promote the activation and function of B cells and killer T cells.

The term "recombinant flagellin" refers to a flagellin polypeptide comprising a peptide epitope embedded within its sequence. A recombinant flagellin is distinct from a classical fusion protein in that the peptide or protein being expressed in a fusion protein is fused to a carrier protein at either its N- or C-terminus, leaving the other terminus free and conformationally unrestrained.

"Amino acid sequence", as used herein, refers to an oligopeptide, peptide, polypeptide, or protein sequence, and fragment thereof, and to naturally occurring or synthetic molecules.

"Avian influenza" or "AI" refers to avian influenza virus that infect birds, including domestic and wild birds. The known avian influenza viruses belong to the H5, H7 and H9 virus subtypes. The avian influenza virus may belong to the low pathogenic (LPAI) or high pathogenic type (HPAI) and may or may not have undergone antigenic shift. Certain strains of avian flu, including H5N1, H7N3, H7N7 and H9N2, have been shown to infect mammals, including humans.

Peptide Epitopes Useful in Preparing a Vaccine

Peptide epitopes derived from influenza proteins are useful in preparing the composition of the present invention. A preferred compositions includes at least one peptide epitope derived from influenza A M1 or M2 proteins in combination with an influenza A or influenza B HA peptide epitope. It is to be noted that peptide epitopes listed herein are provided as for exemplary purposes only. The influenza virus proteins vary between isolates, thereby providing multiple variant sequences for each influenza protein. Accordingly, the present invention encompasses peptide epitopes having one or more amino acid substitutions, additions or deletions.

The matrix protein M1 is a major structural component of the influenza virus particles and forms an inner layer of the lipid cell-derived envelope. Within the virion and in infected cells at late stages of the virus replication, the M1 protein associates with the viral ribonucleoproteins (vRNPs), which are composed of viral RNA molecules, multiple copies of the NP, and the three subunits of the viral polymerase holding the ends of the viral RNAs. The N-terminal domain of M1 refers to amino acids 1 to about amino acid 20 of the M1 protein.

The matrix protein M2 is a hydrogen ion channel resulting in dissociation of the matrix and nucleoprotein complex within vacuoles. This ion channel releases the genome enabling viral RNA to enter the nucleus of the infected cell and initiate viral replication. Therapeutic substances against influenza, such as amantadine and rimantadine act by blocking the M2 activity. Influenza B has a counterpart protein known as NB; although there is no sequence similarity they are both transmembrane proteins and may share similar function. The extracellular domain of the M2 protein which is a transmembrane protein of influenza A virus, is nearly invariant in all influenza A strains. The N-terminal domain of M2 refers to the amino acid sequence N-terminal to the transmembrane domain.

Table 1 provides an exemplary list of M1 and M2 peptide epitopes that may be chosen for preparation of the chimeric proteins of the present invention.

TABLE 1

M1 and M2 peptide epitopes

| Epitope Type* | Epitope Position | Amino Acid Sequence | Nucleotide Sequence | NCBI # |
|---|---|---|---|---|
| | M2 6-9 | EVET (SEQ ID NO: 1) | GAAGTGGAAACC (SEQ ID NO: 81) | ABJ15715.1 |

TABLE 1-continued

M1 and M2 peptide epitopes

| Epitope Type* | Epitope Position | Amino Acid Sequence | Nucleotide Sequence | NCBI # |
|---|---|---|---|---|
| Th | M2 1-15 | MSLLTEVETHTRNGW (SEQ ID NO: 2) | ATGAGCCTGCTGACCGAAGTGGAAACCCACACCAGGAATGGGTGG (SEQ ID NO: 82) | ABJ15715.1 |
| | M2 10-18 | PIRNEWGCR (SEQ ID NO: 3) | CCGATTCGTAACGAATGGGGTTGTCGT (SEQ ID NO: 83) | ABD59884 |
| | M2 8-15 | ETPIRNEWGC (SEQ ID NO: 4) | GAAACCCCGATTCGTAACGAATGGGGTTGTCGT (SEQ ID NO: 84) | ABD59884 |
| | M2 10-20 | PIRNEWGCRCN (SEQ ID NO: 5) | GAAACCCCGATTCGTAACGAATGGGGTTGTCGTGGTTGTCGT (SEQ ID NO: 85) | ABD59884 |
| CTL | M2 3-11 | LLTEVETPI (SEQ ID NO: 6) | CTGCTGACCGAAGTGGAAACCCCGATT (SEQ ID NO: 86) | ABD59884 |
| CTL | M2 2-10 | SLLTEVETP (SEQ ID NO: 7) | AGCCTGCTGACCGAAGTGGAAACCCCG (SEQ ID NO: 87) | ABD59884 |
| CTL | M2 2-11 | SLLTEVETPI (SEQ ID NO: 8) | AGCCTGCTGACCGAAGTGGAAACCCCGATT (SEQ ID NO: 88) | ABD59884 |
| CTL | M2 4-11 | LTEVETPLT (SEQ ID NO: 9) | CTGACCGAAGTGGAAACCCCGCTGACC (SEQ ID NO: 89) | ABD59884 |
| Th | M2 1-15 | MSLLTEVETPIRNEW (SEQ ID NO: 10) | ATGAGCCTGCTGACCGAAGTGGAAACCCCGATTCGCAACGAATGG (SEQ ID NO: 90) | ABD59884 |
| Th | M2 1-18 | MSLLTEVETPIRNEWGCR (SEQ ID NO: 11) | ATGAGCCTGCTGACCGAAGTGGAAACCCCGATTCGCAACGAATGGGGCTGCCGC (SEQ ID NO: 91) | ABD59884 |
| Th | M2 1-15 | MSLLTEVETLTKNGW (SEQ ID NO: 12) | ATGAGCCTGCTGACCGAAGTGGAAACCCTGACCAAAAACGGCTGG (SEQ ID NO: 92) | AAK49250 |
| Th | M2 1-15 | MSLLTEVETLTRNGW (SEQ ID NO: 13) | ATGAGCCTGCTGACCGAAGTGGAAACCCTGACCCGCAACGGCTGG (SEQ ID NO: 93) | ABI85097 |
| CTL | M2 4-12 | LTEVETPIR (SEQ ID NO: 14) | CTGACCGAAGTGGAAACCCCGATTCGC (SEQ ID NO: 94) | ABD59884 |
| CTL | M2 4-13 | LTEVETPIRN (SEQ ID NO: 15) | CTGACCGAAGTGGAAACCCCGATTCGCAAC (SEQ ID NO: 95) | ABD59884 |
| CTL | M2 6-14 | EVETPIRNE (SEQ ID NO: 16) | GAAGTGGAAACCCCGATTCGCAACGAA (SEQ ID NO: 96) | ABD59884 |
| CTL | M2 6-15 | EVETPIRNEW (SEQ ID NO: 17) | GAAGTGGAAACCCCGATTCGCAACGAATGG (SEQ ID NO: 97) | ABD59884 |

TABLE 1-continued

M1 and M2 peptide epitopes

| Epitope Type* | Epitope Position | Amino Acid Sequence | Nucleotide Sequence | NCBI # |
|---|---|---|---|---|
| CTL | M2 4-14 | LTEVETPIRNE (SEQ ID NO: 18) | CTGACCGAAGTGGAAA CCCCGATTCGCAACGA A (SEQ ID NO: 98) | ABD59884 |
| Th | M2 4-18 | LTEVETPIRNEWGC R (SEQ ID NO: 19) | CTGACCGAAGTGGAAA CCCCGATTCGCAACGA ATGGGGCTGCCGC (SEQ ID NO: 99) | ABD59884 |
| B cell | M2 6-13 | EVETPIRN (SEQ ID NO: 20) | GAAGTGGAAACC CCGATTCGTAAC (SEQ ID NO: 100) | ABD59900 |
| B cell | M2 1-18 | MSLLTEVETPTRNE WECR (SEQ ID NO: 21) | ATGAGCCTGCTGACCG AAGTGGAAACCCCGAC CCGCAACGAATGGGAA TGCCGC (SEQ ID NO: 101) | BAD89348 |
| B cell | M2 2-24 | SLLTEVETPTRNEW ECRCS DSSD (SEQ ID NO: 22) | AGCCTGCTGACCGAAG TGGAAACCCCGACCCG CAACGAATGGGAATGC CGCTGCAGCGATAGCA GCGAT (SEQ ID NO: 102) | BAD89348 |
| B cell | M2 2-24 | SLLTEVETPIRNEW GCRCN DSSD (SEQ ID NO: 23) | AGCCTGCTGACCGAAG TGGAAACCCCGATTCG CAACGAATGGGGCTGC CGCTGCAACGATAGCA GCGAT (SEQ ID NO: 103) | ABD59884 |
| B cell | M2 7-15 | VETPIRNEW (SEQ ID NO: 24) | GTGGAAACCCCGATT CGTAACGAATGG (SEQ ID NO: 104) | ABD59884 |
| B cell | M1 2-12 | SLLTEVETYVL (SEQ ID NO: 25) | AGCCTGCTGACCGAAG TGGAAACCTATGTGCT T (SEQ ID NO: 105) | AAO52904 |
| CTL | M1 2-12 | SLLTEVETYVP (SEQ ID NO: 26) | AGCCTGCTGACCGAAG TGGAAACCTATGTGCC G (SEQ ID NO: 106) | AAO33507 |
| CTL | M1 3-11 | LLTEVETYV (SEQ ID NO: 27) | CTGCTGACCGAAGTGG AAACCTATGTG (SEQ ID NO: 107) | AAO33507 |
| CTL | M1 13-21 | SIVPSGPL (SEQ ID NO: 28) | AGCATTGTGCCGAGCG GCCCGCTG (SEQ ID NO: 108) | ABD59901 |
| CTL | M1 17-31 | SGPLKAEIAQRLED V (SEQ ID NO: 29) | AGCGGCCCGCTGAAAG CGGAAATTGCGCAGCG CCTGGAAGATGTG (SEQ ID NO: 109) | ABD59901 |
| CTL | M1 18-29 | GPLKAEIAQRLE (SEQ ID NO: 30) | GGCCCGCTGAAAGCGG AAATTGCGCAGCGCCT GGAA (SEQ ID NO: 110) | ABD59901 |
| CTL | M1 27-35 | RLEDVFAGK (SEQ ID NO: 31) | CGCCTGGAAGATGTGT TTGCGGGCAAA (SEQ ID NO: 111) | ABD59901 |
| CTL | M1 41-51 | ALMEWLKTRPI (SEQ ID NO: 32) | GCGCTGATGGAATGGC TGAAAACCCGCCCG (SEQ ID NO: 112) | ABD59901 |

TABLE 1-continued

M1 and M2 peptide epitopes

| Epitope Type* | Epitope Position | Amino Acid Sequence | Nucleotide Sequence | NCBI # |
|---|---|---|---|---|
| CTL | M1 50-59 | PILSPLTKGI (SEQ ID NO: 33) | CCGATTCTGAGCCCGC TGACCAAAGGCATT (SEQ ID NO: 113) | ABD59901 |
| CTL | M1 51-59 | ILSPLTKGI (SEQ ID NO: 34) | ATTCTGAGCCCGCTGA CCAAAGGCATT (SEQ ID NO: 114) | ABD59901 |
| CTL | M1 55-73 | LTKGILGFVFTLTV PSERG (SEQ ID NO: 35) | CTGACCAAAGGCATTC TGGGCTTTGTGTTTAC CCTGACCGTGCCGAGC GAACGCGGC (SEQ ID NO: 115) | ABD59901 |
| CTL | M1 56-68 | TKGILGFVFTLTV (SEQ ID NO: 36) | ACCAAAGGCATTCTGG GCTTTGTGTTTACCCT GACCGTG (SEQ ID NO: 116) | ABD59901 |
| CTL | M1 57-68 | KGILGFVFTLTV (SEQ ID NO: 37) | AAAGGCATTCTGGGCT TTGTGTTTACCCTGAC CGTG (SEQ ID NO: 117) | ABD59901 |
| CTL | M1 58-66 | GILGFVFTL (SEQ ID NO: 38) | GGCATTCTGGGCTTTG TGTTTACCCTG (SEQ ID NO: 118) | ABD59901 |
| CTL | M1 60-68 | LGFVFTLTV (SEQ ID NO: 39) | CTGGGCTTTGTGTTTA CCCTGACCGTG (SEQ ID NO: 119) | ABD59901 |
| CTL | M1 59-67 | ILGFVFTLT (SEQ ID NO: 40) | ATTCTGGGCTTTGTGT TTACCCTGACC (SEQ ID NO: 120) | ABD59901 |
| CTL | M1 128-135 | ASCMGLIY (SEQ ID NO: 41) | GCGAGCTGCATGGGCC TGATTTAT (SEQ ID NO: 121) | ABD59901 |
| CTL | M1 134-142 | RMGAVTTEV (SEQ ID NO: 42) | CGCATGGGCGCGGTGA CCACCGAAGTG (SEQ ID NO: 122) | ABD59901 |
| CTL | M1 145-155 | GLVCATCEQIA (SEQ ID NO: 43) | GGCCTGGTGTGCGCGA CCTGCGAACAGATTGC G (SEQ ID NO: 123) | ABD59901 |
| CTL | M1 164-172 | QMVATTNPL (SEQ ID NO: 44) | CAGATGGTGGCGACCA CCAACCCGCTG (SEQ ID NO: 124) | ABD59901 |
| CTL | M1 164-173 | QMVATTNPLI (SEQ ID NO: 45) | CAGATGGTGGCGACCA CCAACCCGCTGATT (SEQ ID NO: 125) | ABD59901 |
| CTL | M1 178-187 | RMVLASTTAK (SEQ ID NO: 46) | CGCATGGTGCTGGCGA GCACCACCGCGAAA (SEQ ID NO: 126) | ABD59901 |
| CTL | M1 232-240 | DLLENLQTY (SEQ ID NO: 47) | GATCTGCTGGAAAACC TGCAGACCTAT (SEQ ID NO: 127) | ABD59901 |

Nucleoprotein (NP) is one of the groups of specific antigens, which distinguishes between influenza A, B and C viruses. In contrast to HA, NP is highly conserved, being 94% conserved in all influenza A viruses. Influenza A virus NP-specific antibody has no virus neutralizing activity, but NP is an important target for cytotoxic T lymphocytes (CTL) which are c and for the poor control of infection by immunization (Ada and Jones, 1986).

The influenza virus RNA polymerase is a heterocomplex composed of the three polymerase (P) proteins PB1, PB2 and PA-present in a 1:1:1 ratio. Their role in influenza virulence has not been fully elucidated. Non-limiting examples of HA, NP and PB peptide epitopes can be found in table 2 herein below.

TABLE 2

HA, NP and PB peptide epitopes.

| Epitope Type* | Epitope Position | Amino Acid Sequence | Nucleotide Sequence | NCBI accession |
|---|---|---|---|---|
| B cell | HA 91-108 | SKAYSNCYPYDVPD YASL (SEQ ID NO: 48) | AGCAAAGCTTACAGCAAC TGTTACCCTTAT GATGTGCCGGATTAT GCCTCCCTT (SEQ ID NO: 128) | AAM82562 |
| B cell | HA 91-108 | SKAFSNCYPYDVPD YASL (SEQ ID NO: 49) | AGCAAAGCGTTTAGCAAC TGCTATCCGTATGATGTG CCGGATTATGCGAGCCTG (SEQ ID NO: 129) | CAC81017 |
| B cell | HA 107-124 | STAYSNCYPYDVPD YASL (SEQ ID NO: 50) | AGCACCGCGTATAGCAAC TGCTATCCGTATGATGTG CCGGATTATGCGAGCCTG (SEQ ID NO: 130) | ABD59854 (from A/ TW/3286/ 03 (H3N2) |
| B cell | HA 166-175 (HA 150-159 A/PR/8 strain) | WLTEKEGSYP (SEQ ID NO: 51) | TGGCTGACGGAGAAG GAGGGCTCATACCCA (SEQ ID NO: 131) | ABD77675 |
| Th | HA 306-324 | PKYVKQNTLKLATG MRNVP (SEQ ID NO: 52) | CCCAAGTATGTTAAGCAA AACACTCTGAAGTTGGCA ACAGGGATGCGGAATGTA CCAGAGAAACAAACTAGA GGC (SEQ ID NO: 132) | AAL62329 |
| CTL | HA 521-531 | GVKLESMGIYQ (SEQ ID NO: 53) | GGCGTGAAACTGGAAAGC ATGGGCATTTATCAG (SEQ ID NO: 133) | ABJ09518 |
| CTL | HA 518-528 | EISGVKLESNG (SEQ ID NO: 54) | GAAATTTCCGGCGTGAAA CTGGAAAGCATGGGC (SEQ ID NO: 134) | ABJ09518 |
| CTL | HA 458-467 | NVKNLYEKVK (SEQ ID NO: 55) | AACGTGAAAAACCTGTAT GAAAAAGTGAAA (SEQ ID NO: 135) | ABD77675 |
| Th | HA 128-145 | KVKILPKDRWTQHT TTGG (SEQ ID NO: 56) | AAAGTGAAAATTCTGCCG AAAGATCGCTGGACCCAG CATACCACCACCGGCGGC (SEQ ID NO: 136) | AAO46269 |
| Th | HA 307-319 (HA 306-318) | PKYVKQNTLKLAT (SEQ ID NO: 57) | CCCAAGTATGTTAAGCAA AACACTCTGAAGTTGGCA ACA (SEQ ID NO: 137) | AAL62329 |
| Th | NP 91-99 | KTGGPIYRR (SEQ ID NO: 58) | AAAACTGGAGGACCT ATATACAGGAGAGG (SEQ ID NO: 138) | BAA99400 |
| CTL | NP 44-52 | CTELKLSDY (SEQ ID NO: 59) | TGCACCGAACTGAAACTG AGCGATTAT (SEQ ID NO: 139) | BAA99400 |
| CTL | NP 82-95 | HPSAGKDPKKTGGP (SEQ ID NO: 60) | CATCCGAGCGCGGGCAAA GATCCGAAAAAACCGGC GGCCCG (SEQ ID NO: 140) | BAA99400 |
| CTL | NP 82-94 | HPSAGKDPKKTGG (SEQ ID NO: 61) | CATCCGAGCGCGGGCAAA GATCCGAAAAAACCGGC GGC (SEQ ID NO: 141) | BAA99400 |

TABLE 2-continued

HA, NP and PB peptide epitopes.

| Epitope Type* | Epitope Position | Amino Acid Sequence | Nucleotide Sequence | NCBI accession |
|---|---|---|---|---|
| Th | NP 206-229 | FWRGENGRKTRSAY ERMCNILKGK (SEQ ID NO: 62) | TTTTGGCGCGGCGAAAAC GGCCGCAAAACCCGCAGC GCGTATGAACGCATGTGC AACATTCTGAAAGGCAAA (SEQ ID NO: 142) | ABD59868 |
| CTL | NP 265-273 | ILRGSVAHK (SEQ ID NO: 63) | ATTCTGCGCGGCAGCGTG GCGCATAAA (SEQ ID NO: 143) | BAA99400 |
| CTL | NP 305-313 | KLLQNSQVY (SEQ ID NO: 64) | AAACTGCTGCAGAACAGC CAGGTGTAT (SEQ ID NO: 144) | ABD59868 |
| CTL | NP 335-349 | SAAFEDLRVLSFIR G (SEQ ID NO: 65) | AGCGCGGCGTTTGAAGAT CTGCGCGTGCTGAGCTTT ATTCGCGGC (SEQ ID NO: 145) | ABD35694 |
| CTL | NP 335-350 | SAAFEDLRVSSFIR GT (SEQ ID NO: 66) | AGCGCGGCGTTTGAAGAT CTGCGCGTGAGCAGCTTT ATTCGCGGCACC (SEQ ID NO: 146) | ABK34765 |
| CTL | NP 335-350 | SAAFEDLRVLSFIR GY (SEQ ID NO: 67) | AGCGCGGCGTTTGAAGAT CTGCGCGTGCTGAGCTTT ATTCGCGGCTAT (SEQ ID NO: 147) | ABD35694 |
| CTL | NP 380-393 | ELRSRYWAIRTRSG (SEQ ID NO: 68) | GAACTGCGCAGCCGCTAT TGGGCGATTCGCACCCGC AGCGGC (SEQ ID NO: 148) | ABK34765 |
| CTL | NP 380-388 | ELRSRYWAI (SEQ ID NO: 69) | GAACTGCGCAGCCGCTAT TGGGCGATT (SEQ ID NO: 149) | ABK34765 |
| CTL | NP 383-391 | SRYWAIRTR (SEQ ID NO: 70) | AGCCGCTATTGGGCGATT CGCACCCGC (SEQ ID NO: 150) | BAA99400 |
| CTL | NP 384-394 | YWAIRTRSGG (SEQ ID NO: 71) | TATTGGGCGATTCGCACC CGCAGCGGCGGC (SEQ ID NO: 151 | BAA99400 |
| CTL | NP 382-390 | SRYWAIRTR (SEQ ID NO: 72) | AGCCGCTATTGGGCGATT CGCACCCGC (SEQ ID NO: 152) | BAA99400 |
| CTL | NP 418-426 | LPFDKPTIM (SEQ ID NO: 73) | CTGCCGTTTGATAAACCG ACCATTATG (SEQ ID NO: 153) | BAA99400 |
| CTL | PB1 591-599 | VSDGGPNLY (SEQ ID NO: 74) | GTGAGCGATGGCGGCCCG AACCTGTAT (SEQ ID NO: 154) | ABK34974 |
| CTL | PB1 571-579 | RRSFELKKL (SEQ ID NO: 75) | CGCCGCAGCTTTGAACTG AAAAAACTG (SEQ ID NO: 155) | ABK34974 |
| CTL | PB2 368-376 | RRATAILRK (SEQ ID NO: 76) | CGCCGCGCGACCGCGATT CTGCGCAAA (SEQ ID NO: 156) | ABK34762 |

In some embodiments the vaccine further comprises a peptide epitope derived from influenza B. Non-limiting examples of influenza B peptide epitopes are shown in Table 3.

TABLE 3

Influenza B peptide epitopes

| Epitope type* | Epitope position | Amino acid sequence | Nucleotide sequence | NCBI accession |
|---|---|---|---|---|
| CTL | NP 30-38 (flu B) | RPIIRPATL (SEQ ID NO: 77) | CGCCCGATTATTCGCCC GGCGACCCTG (SEQ ID NO: 157) | ABF21293 |
| CTL | NP 263-271 (flu B) | ADRGLLRDI (SEQ ID NO: 78) | GCAGATAGAGGGCTA TTGAGAGACATC (SEQ ID NO: 158) | ABF21293 |
| Th | HA 308-320 (flu B) | PYYTGEHAKAIGN (SEQ ID NO: 79) | CCGTATTATACCGGCGA ACATGCGAAAGCGATTG GCAAC (SEQ ID NO: 159) | ABI84095 |
| B | HA 354-372 (flu B) | PAKLLKERGFFGAI AGFLE (SEQ ID NO: 80) | CCGGCGAAACTGCTGAA AGAACGCGGCTTTTTG GCGCGATTGCGGGCTTT CTGGAA (SEQ ID NO: 160) | ABI83926 |

*Each peptide may belong to one or more epitope types. For example, a peptide that elicits a B-cell response can also elicit a T-cell (Th and/or CTL) response.

Nucleic Acids

The present invention further provides nucleic acid molecules encoding the a vector such as an expression vector comprising the influenza epitopes and a host cell comprising a vector which comprises an influenza epitope useful in the preparation of a synthetic vaccine of the invention.

An isolated nucleic acid sequence encoding a peptide can be obtained from its natural source, for example as a portion of a gene. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, comprising, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional flagellin of the present invention.

A polynucleotide or oligonucleotide sequence can be deduced from the genetic code of a protein, however, the degeneracy of the code must be taken into account, and nucleic acid sequences of the invention also include sequences, which are degenerate as a result of the genetic code, which sequences may be readily determined by those of ordinary skill in the art.

The terms "nucleic acid" and "polynucleotide" as used herein refer to an oligonucleotide, polynucleotide or nucleotide and fragments or portions thereof, and to DNA or RNA of genomic or synthetic origin, which may be single- or double-stranded, and represent the sense or antisense strand. The term should also be understood to include, as equivalents, analogs of either RNA or DNA made from nucleotide analogs, and, as applicable to the embodiment being described.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art. The oligonucleotides encoding the specific peptide epitopes useful in the preparation of the vaccine of the present invention are provided in tables 1-3 hereinabove.

As used herein, highly stringent conditions are those, which are tolerant of up to about 5% to about 25% sequence divergence, preferably up to about 5% to about 15%. Without limitation, examples of highly stringent (−10° C. below the calculated Tm of the hybrid) conditions use a wash solution of 0.1×SSC (standard saline citrate) and 0.5% SDS at the appropriate Ti (incubation temperature) below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 μg/ml denatured, fragmented salmon sperm DNA at an appropriate Ti. (See generally Sambrook et al., Molecular Cloning: A Laboratory Manual, 2d edition, Cold Spring Harbor Press (1989) for suitable high stringency conditions).

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti of about 20° C.-25° C. below Tm for DNA:DNA hybrids and about 10° C.-15° C. below Tm for DNA:RNA hybrids. It is also maximized by an ionic strength of about 1.5M $Na^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any). The Tm of a perfect hybrid may be estimated for DNA:DNA hybrids using the equation of Meinkoth et al (1984).

Chimeric or Recombinant Molecules

A "chimeric protein", "chimeric polypeptide" or "recombinant protein" are used interchangeably and refer to an influenza peptide epitope operatively linked to a polypeptide other than the polypeptide from which the peptide epitope was derived. The peptide epitopes of the present invention can be prepared by expression in an expression vector as a chimeric protein. The methods to produce a chimeric or recombinant protein comprising an influenza peptide epitope are known to those with skill in the art. A nucleic acid sequence encoding an influenza peptide epitope can be inserted into an expression vector for preparation of a polynucleotide construct for propagation and expression in host cells.

In a non-limiting example, the chimeric polypeptide of the present invention includes chimeras of an influenza peptide epitope with one of the following polypeptides: flagellin, Cholera toxin, Tetanus toxin, Ovalbumin, Tuberculosis heat shock protein, Diphtheria Toxoid, Protein G from respiratory syncytial virus, Outer Membrane Protein from *Neisseria meningitides*, nucleoprotein (N) of vesicular stomatitis virus, glycoprotein (G) of vesicular stomatitis virus, *Plasmodium falciparum* Antigen Glutamate-Rich Protein, Merozoite Surface Protein 3 or Viruses envelope (E) protein.

The term "expression vector" and "recombinant expression vector" as used herein refers to a DNA molecule, for example a plasmid, flagellin or virus, containing a desired and appropriate nucleic acid sequences necessary for the expression of the recombinant peptide epitopes for expression in a particular host cell. As used herein "operably linked" refers to a functional linkage of at least two sequences. Operably linked includes linkage between a promoter and a second sequence, for example an nucleic acid of the present invention, wherein the promoter sequence initiates and mediates transcription of the DNA sequence corresponding to the second sequence.

The regulatory regions necessary for transcription of the peptide epitope can be provided by the expression vector. The precise nature of the regulatory regions needed for gene expression may vary among vectors and host cells. Generally, a promoter is required which is capable of binding RNA polymerase and promoting the transcription of an operably-associated nucleic acid sequence. Regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites. A translation initiation codon (ATG) may also be provided.

In order to clone the nucleic acid sequences into the cloning site of a vector, linkers or adapters providing the appropriate compatible restriction sites during synthesis of the nucleic acids. For example, a desired restriction enzyme site can be introduced into a fragment of DNA by amplification of the DNA by use of PCR with primers containing the desired restriction enzyme site.

An expression construct comprising a peptide epitope sequence operably associated with regulatory regions can be directly introduced into appropriate host cells for expression and production of the peptide epitopes per se or as recombinant fusion proteins. The expression vectors that may be used include but are not limited to plasmids, cosmids, phage, phagemids, flagellin or modified viruses. Typically, such expression vectors comprise a functional origin of replication for propagation of the vector in an appropriate host cell, one or more restriction endonuclease sites for insertion of the desired gene sequence, and one or more selection markers.

The recombinant polynucleotide construct comprising the expression vector and a peptide epitope should then be transferred into a bacterial host cell where it can replicate and be expressed. This can be accomplished by methods known in the art. The expression vector is used with a compatible prokaryotic or eukaryotic host cell which may be derived from bacteria, yeast, insects, mammals and humans.

A particularly preferred expression vector is a flagellin vector. A non-limiting example of a flagellin expression vector is disclosed in U.S. Pat. No. 6,130,082 incorporated herein by reference. Other expression vectors which include a flagella gene, for example a *salmonella* fliC gene are also suitable. The host cells which express the recombinant flagellin can be formulated as live vaccines.

An alternative to producing the peptide epitopes by recombinant techniques is peptide synthesis by use of a peptide synthesizer. Conventional peptide synthesis or other synthetic protocols well known in the art may be used.

Vaccine Formulation

The vaccine can be formulated for administration in one of many different modes. According to one embodiment of the invention, the vaccine is administered intranasally. The intranasal composition can be formulated, for example, in liquid form as nose drops, spray, or suitable for inhalation, as powder, as cream, or as emulsion. The composition can contain a variety of additives, such as adjuvant, excipient, stabilizers, buffers, or preservatives. For straightforward application, the vaccine composition is preferably supplied in a vessel appropriate for distribution of the recombinant flagellin in the form of nose drops or an aerosol. In certain preferred embodiments the vaccine is formulated for mucosal deliver, in particular nasal delivery (Arnon, 2001; Ben-Yedidia, 1999).

In another embodiment of the invention, administration is oral and the vaccine may be presented, for example, in the form of a tablet or encased in a gelatin capsule or a microcapsule.

In yet another embodiment, the vaccine is formulated for parenteral administration. In some embodiments the vaccine is formulated for mass inoculation, for example for use with a jet-injector or a single use cartridge.

The formulation of these modalities is general knowledge to those with skill in the art.

The liposome provides another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 500 μm. Liposomes have been found to be effective in delivering therapeutic agents to dermal and mucosal surfaces. Liposomes can be further modified for targeted delivery by for example, incorporating specific antibodies into the surface membrane, or altered to encapsulate bacteria, viruses or parasites. The average survival time of the intact liposome structure can be extended with the inclusion of certain polymers, for example polyethylene glycol, allowing for prolonged release in vivo.

Microparticles and nanoparticles employ small biodegradable spheres which act as depots for vaccine delivery. The major advantage that polymer microspheres possess over other depot-effecting adjuvants is that they are extremely safe and have been approved by the Food and Drug Administration in the US for use in human medicine as suitable sutures and for use as a biodegradable drug delivery system (Langer, 1990). The rates of copolymer hydrolysis are very well characterized, which in turn allows for the manufacture of microparticles with sustained antigen release over prolonged periods of time (O'Hagen, et al., 1993).

Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 μm to 200 μm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers.

In some applications an adjuvant or excipient may be included in the vaccine formulation. The choice of the adjuvant will be determined in part by the mode of administration of the vaccine. For example, non-injected vaccination will lead to better overall compliance and lower overall costs. A preferred mode of administration is intranasal administration. Non-limiting examples of intranasal adjuvants include chitosan powder, PLA and PLG microspheres, QS-21, calcium phosphate nanoparticles (CAP) and mCTA/LTB (mutant cholera toxin E112K with pentameric B subunit of heat labile enterotoxin).

Therapeutic Use of Vaccine

The vaccines of the invention are intended both for use in humans and in animals including livestock, poultry and domestic animals, for prevention or attenuation of influenza A and B disease.

The present invention provides a method for inducing an immune response against influenza virus. The method comprises administering to a subject, which is an animal or a human subject, a vaccine comprising recombinant flagellin according to the principles of the present invention.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

ABBREVIATIONS: Ab: Antibodies; CTL: Cytotoxic T-lymphocytes; EID: Egg-infective dose; HA: Hemagglutinin; HAU: Hemagglutination unit; NP: Nucleoprotein; PMBC: Peripheral blood mononuclear cells; Th: T helper; IN or i.n.: intranasal; IP: intraperitoneal; IM or i.m.: intramuscular; NK: natural killer cells; E:T ratio: effector target ratio.

Example 1

Synthesis of Peptides and Recombinant Flagellin

The epitopes may be expressed as recombinant flagella, wherein each flagella comprises one or more peptide epitopes. Alternatively, the peptide epitopes can be expressed in an expression vector as a multimeric fusion protein comprising two or more peptide epitopes.

The recombinant flagellin are synthesized by molecular biology methods known in the art. In brief: a flagella expression vector comprising an antibiotic marker was prepared. The synthesized oligonucleotides were inserted at the EcoRV site of the plasmid and transfected into *E. coli* competent cells. Colonies containing the recombinant plasmid were selected by probing with a radiolabeled oligonucleotide. Plasmids from positive colonies were purified and the insert orientation was determined using restriction analysis. The desired plasmids were used to transform *Salmonella typhimurium* LB5000 (a restrictive negative, modification proficient non flagellated) competent cells and were then transferred to a flagellin negative live vaccine strain (an Aro A mutant) of *Salmonella dublin* SL5928 by transduction using the phage P22HT105/1 int. The transformed *S. dublin* were selected for kanamycin resistance, motility under the light microscope and growth in semisolid LB agar plates, supplemented with Oxoid nutrient broth no. 2. Selected clones were grown overnight in 2 liters of medium and the flagellin purified by acidic cleavage. The resulting product is an aggregate of the flagellin and may be used as such for a vaccine.

The recombinant flagellin is not intended to be limited by the choice of the flagellin sequence. In some embodiments the flagellin having accession number X03395 *Salmonella* muenchen H1-d gene for phase-1-d flagellin (ATCC 8388).

Example 2

Response of Chimeric Mice to Whole Inactivated Influenza Virus

Human mouse chimeras are used to evaluate the immunogenic response elicited by the vaccine of the present invention. In order to establish the suitability of the human/mouse radiation chimera for evaluating the peptide-based vaccine, their immune response to inactive purified influenza virus was evaluated. The mice were immunized i. p. with 50 μg of the virus on the day of PBMC transplantation, followed by a sublethal viral challenge with influenza A/Texas/1/77 strain 14 days after immunization. The vaccination of human/mouse radiation chimera with the whole killed virus vaccine, without any adjuvant, induced production of specific antibodies—the serum antibody titer was significantly higher (2.4 fold) in the immunized chimera as compared to the control group. Moreover, this vaccination markedly reduced the subsequent virus infection. The lung virus titer after challenge was significantly lower (by 2.7 orders of magnitude) in the immunized chimera as compared to the control group.

This experiment demonstrates the suitability of the human/mouse radiation chimera for evaluating the anti-influenza response following immunization.

Example 3

FACS Analysis of Immunized Mice for Evaluating the Engraftment of Human PBMC in Human/BALB Chimera The successful engraftment of the human cells in the human/mouse chimeras demonstrated in a preliminary experiment showing that most of the lymphocytes in the peritoneum (50-80%) and in the lungs of the mice (30-60%) were of human origin. For the evaluation of human cell engraftment in the human/mouse chimera, the presence of human cells in the engrafted mice was analyzed by FACS.

Example 4

Virus Clearance from the Lungs Following Sub-Lethal Challenge

Influenza infection is a respiratory disease; hence, a local immune response induced by an intranasal administration of the vaccine may be more efficient than parenteral administration. The immunization schedule was modified in order to adapt it for intranasal immunization.

Mice (6-8 per group in 7 repeated experiments) are immunized intranasally (i. n.) 10-12 days after PBMC transplantation, as described in the Methods. Ten days later, they are challenged i. n. with 10-4 HAU in 50 µl allantoic fluid of live A/Texas/1/77 strain or another strain of influenza virus. Five days later they were sacrificed and their lungs were removed for virus titration. Human antibody production in these mice is evaluated in both the serum (before challenge) and in the lungs (after challenge).

Further to the sub-lethal infection challenge experiment, the ability of the vaccine to protect human/mouse chimera from a lethal dose of influenza virus is examined.

Example 5

Protection from Infection with Different Strains of Influenza

One of the major problems with currently available influenza vaccines is that they are effective only against the strains included in the vaccine. Therefore, it is of interest to examine the ability of the recombinant flagellin comprising influenza epitopes to protect mice from different influenza subtypes. In one embodiment the M peptide epitope, which is expressed in the flagellin, is conserved in all influenza H3 subtypes, while the T-cell epitopes are from regions of the haemagglutinin and nucleoprotein highly conserved in other subtypes as well. In other examples the M peptide epitope is conserved in all H9 or H5 strains. In the first step, it is shown that rabbit antibodies towards these epitopes can indeed recognize and react in ELISA with different strains of influenza including A/Texas/1/77, A/Aichi/68, A/PR/8/34 and A/Japanese/57. To further test the potential of these epitopes to confer cross protection in humans, the human/mouse radiation chimera (8 mice per group) were immunized i. n. with the recombinant flagellin. Their resistance to different influenza strains challenge was detected 7 days later and compared to non-transplanted mice that are immunized with the same flagella mixture. The influenza strains used for infection were: A/Texas/1/77 (H3N2), A/Japanese/57 (H2N2) and A/PR/8/34 (H1N1). Other strains are tested, as well.

Example 6

CTL Response Assay

Following immunization with the vaccine of the present invention, the animals' spleens are removed and incubated with the peptide representing the relevant epitope (for example NP 335-350 or M2 1-18) for an additional 5 days. TAP deficient syngeneic target cells (with the same HLA A2.1 typing, for example: RMA cells) are incubated with the same peptide and with $S^{35}$-Methionine in a separate dish. The activated splenocytes are incubated with the target cell and upon recognition of the peptide, will attack them and release of methionine. High radioactivity counts indicate a high level of active CTL cells.

Example 7

Serum Antibody and Antibody Neutralization Assays

Mice, guinea pigs or rabbits are immunized with the mixture of recombinant flagellin, 14 days post immunization, blood samples are taken and serum is separated. These sera can be employed for detection the specificity of the antibodies, for example by ELISA or western blot, in addition, it is possible to determine their type, i.e. IgG1, or IgG2a or IgG2c etc. In lung homogenates IgA can be detected, indicative of a mucosal immune response.

Neutralization assay: MDCK cells are infected by influenza virus as determined by plaque counts or by MTT (sort of viability staining), following incubation of the virus with serum from immunized animals; the antibodies bind the virus and prevent infection of the MDCK cells. A reduced number of plaques or increased viability of the cells indicate the specificity of the antibodies and their ability to prevent/reduce infection.

Example 8

Immunogenicity of Individual Epitopes

HHD/HLA A2 transgenic mice were immunized with flagella expressing each epitope (Fla-91, Fla-335, Fla-380, Fla-M1 2-12) or with a mixture of 6 epitopes (Hexa-vaccine1: Fla-91, Fla-335, Fla-380, Fla-M1 2-12, Fla-354 and Fla-307). Fla-91 refers to flagella comprising HA 91-108 epitope; Fla-335 refers to flagella comprising NP 335-350 epitope; Fla-380 refers to flagella comprising NP 380-393 epitope; Fla-M1 2-12 refers to flagella expressing M1 2-12 epitope; Fla-354 refers to flagella expressing HA 354-372 (influenza B) epitope; Fla-307 refers to flagella expressing HA 307-319 epitope.

The cells were incubated with the respective peptide and the cells from Hexa-vaccine immunized mice were incubate with the 4 peptides HA91, NP335, NP380, M1 2-12. The peptide epitope sequences, sequence identifiers and strain homology data can be founds in table 4 herein below.

TABLE 4

Hexa vaccine1 peptide epitope list

| Epitope type | Epitope sequence | Homology in Influenza strains |
|---|---|---|
| Th | HA 307-319 PKYVKQNTLKLAT (SEQ ID NO: 57) | H3N2 |
| CTL | NP 335-350 SAAFEDLRVLSFIRGY (SEQ ID NO: 67) | H1N2, H2N2, H3N2, H9N2. |
| CTL | NP 380-393 ELRSRYWAIRTRSG (SEQ ID NO: 68) | H1N1, H1N2, H2N2, H3N8, H5N1, H5N2, H5N9, H6N1, H6N2, H6N9, H7N7, H9N2, H9N2, H11N1, H11N8, H11N9, H14N5. |
| B-cell | HA 91-108 SKAYSNCYPYDVPDYASL (SEQ ID NO: 48) | H3N2 |
| B-cell and CTL | M1 2-12 SLLTEVETYVP (SEQ ID NO: 26) | H1N1, H3N2, H4N6, H5N1, H5N2, H5N3, H6N1, H7N3, H9N2, |

TABLE 4-continued Hexa vaccine1 peptide epitope list

| Epitope type | Epitope sequence | Homology in Influenza strains |
|---|---|---|
| B-cell (Influenza B) | HA 354-372 PAKLLKERGFFGAIAGFLE (SEQ ID NO: 80) | B/HongKong/330/2001; B/Beijing/1/87; B/Singapore/222/79; B/Oregon/5/80; B/Shangdong/7/97; B/Memphis/13/03; B/Los Angeles/1/02; B/Nebraska/1/01; B/Hong Kong/548/2000; B/Hong Kong/156/99; B/Vienna/1/99; B/Lee/40 and others |

Immunogenicity in "HHD Transgenic Mouse" Model

The CTL epitopes were selected for their binding to HLA-A2 molecules. In order to study HLA-restricted responses, the D b−/− β2 microglobulin (β2m) null mice, transgenic for a recombinant HLA-A2.1/D b−/−. β2 microglobulin single chain (HHD mice) was employed. These mice combine classical HLA transgenesis with selective destruction of murine H-2 and show only HLA-A2.1-restricted responses. These mice serve as an animal model for research of systems involving cellular immunity such as cancer, autoimmunity and vaccination issues.

The cellular response that contributes to the elimination of the virus involves cytokine-mediated mechanisms. The involvement of cytokines in the immune response mounted by the recombinant vaccine was studied in the HHD transgenic mice model.

In this study, flagella expressing various peptide epitopes in PBS, emulsified in Freund adjuvant, were administered subcutaneously three times. The control group was administered with PBS emulsified in Freund adjuvant.

Cellular assays: splenocytes of these mice were incubated in the presence of the synthetic peptides corresponding to the above epitope. IFN-γ secretion by the cells in response to the stimulation with the peptides was monitored by ELISA.

Figure 1:
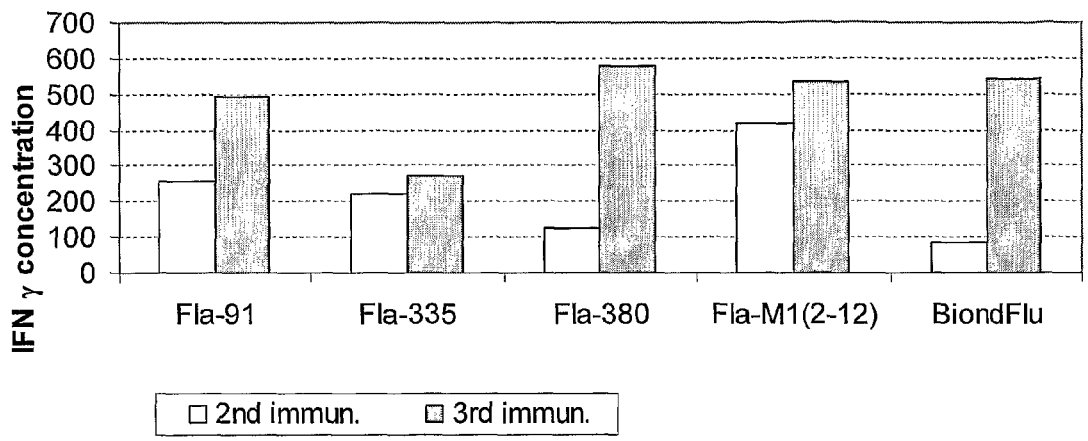

FIG. 1 shows the IFN gamma secretion as measured from lymphocytes incubated with the respective peptide after the second and third immunization.

Activated lymphocytes secreted IFN-γ in response to incubation with the corresponding peptides. The group immunized with Hexa-vaccine1, containing the mixture of 6 recombinant flagella was incubated with a mixture of the 4 cellular epitopes tested separately. After the third immunization, The IFN-γ secretion from these cells is significantly elevated (IFN levels secreted by cells incubated with medium, were below the assay detection level of 2 pg/ml). The IFN gamma secreted from non activated lymphocytes (negative controls—grown in medium without peptide) was <0.004 ng/ml.

NK (Natural Killer cell) lysis contributes to the anti viral response. It is known that viral infected cells are more sensitive to lysis than non-infected cells. It is speculated that the recognition of target cells by NK cells is more 'specific' than previously thought. A similarity in peptide motif between HLA A2 binders and HLA-G (expressed on NK cells) binders has been demonstrated.

Therefore, in addition to the non-specific mechanism of NK activation, peptides specific to HLA-A2 can elicit further specific elevation of NK activity (lysis).

Cytotoxic T lymphocyte (CTL) assays: HHD/HLA A2.1 mice were immunized with Hexa-vaccine1 in PBS. Direct lysis of target cells by CD8+ lymphocytes was not demonstrated, however, a marked lysis of Yac-1 cells that are sensitive to NK lysis was obtained. Lysis by NK was found after the second immunization and was further elevated after the third immunization. It should be noted that baseline levels of NK activation in naïve mice is approximately null.

Figure 2A:
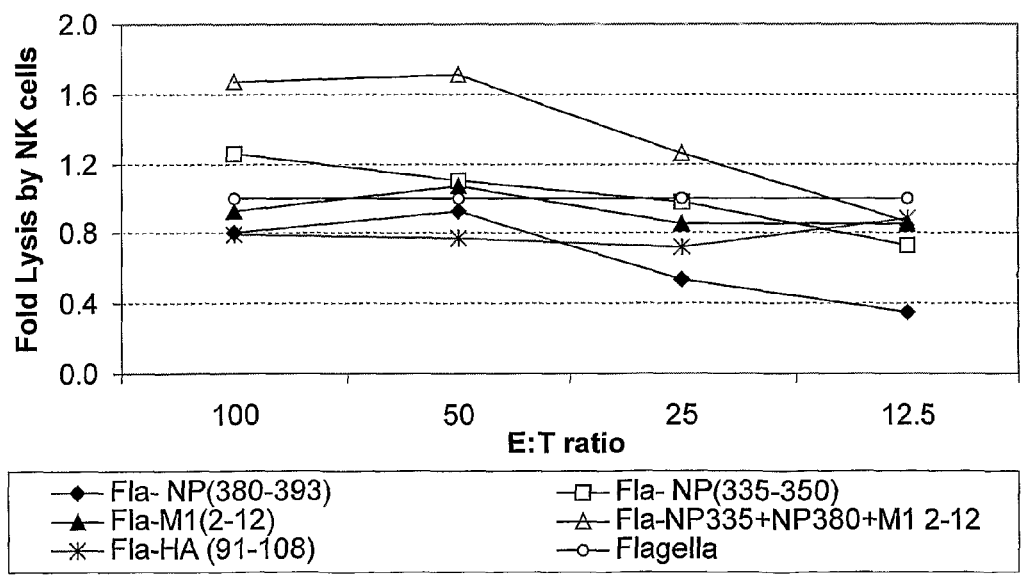
Figure 2B:
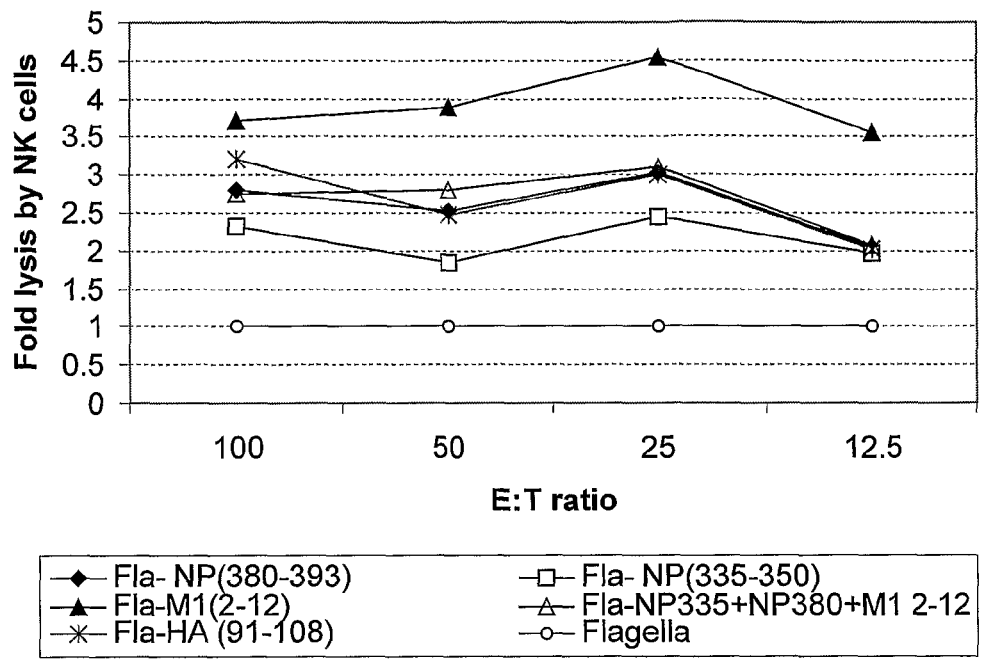
Figure 2C:
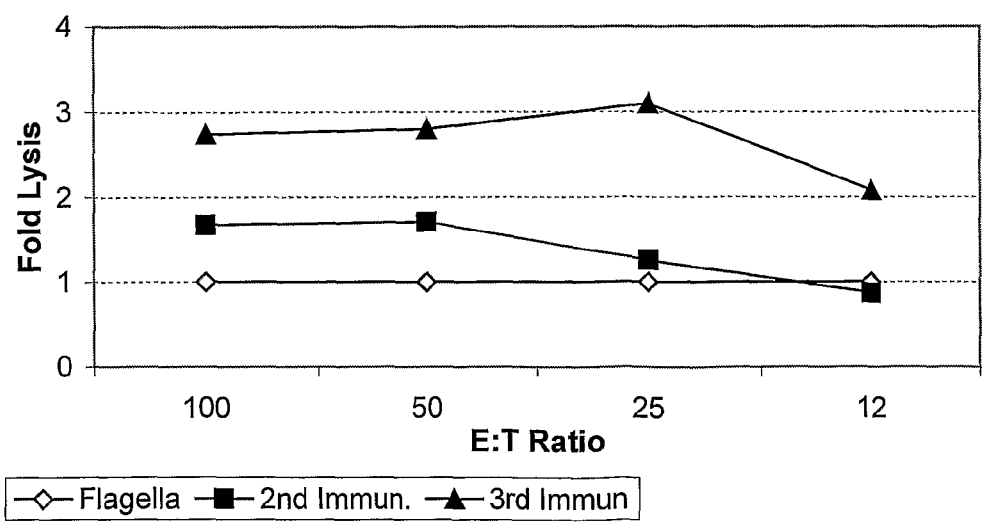

FIGS. 2A-2C shows lysis of target cells by NK derived from vaccinated mice was followed after the second and third immunization. Percentage of lysis of YAC-1 targets by NK cells after the second and third immunization is presented. Splenic lymphocytes from immunized mice were sensitized with the peptides included in the recombinant flagella for 5 days and then incubated with $^{35}$S-Met labeled YAC-1 cells. Specific lysis was determined at different E:T ratios. The data (% lysis by NK cells of each group) is presented as fold activation in comparison to the lysis of the group immunized with native flagella. After the second immunization, NK cells from the mice immunized with the combination of 6 epitopes (Hexa-vaccine1) were able to lyse the target cells more efficiently than the cells from mice vaccinated with the native flagella. FIGS. 2A and 2B show the NK cell lysis of individual recombinant peptide epitopes or a combination of three recombinant epitopes (Fla-NP335, Fla-NP380, Fla-M1 2-12).

After three immunizations, the cells from mice immunized with M1 2-12 showed a significant elevation in their ability to destroy target cells. The M1 2-12 peptide epitope is therefore a useful peptide epitope in the preparation of the vaccine of the present invention.

Figure 3A:
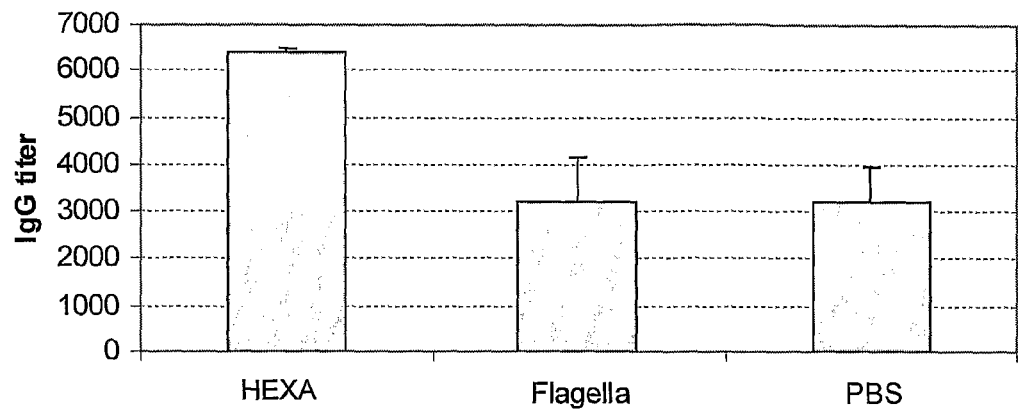
Figure 3B:
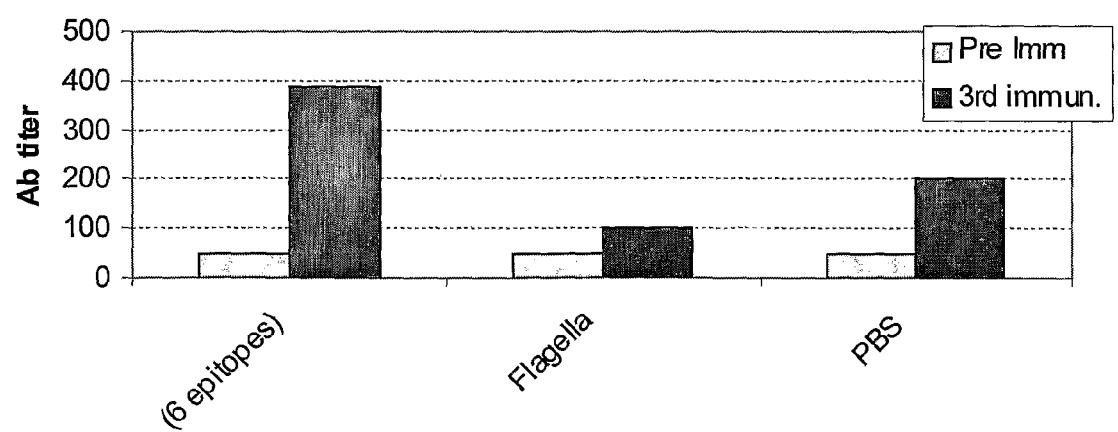

FIGS. 3A and 3B show the results of immunization of C57Bl/6 mice with the Hexa-vaccine1, consisting of flagella with 6 influenza epitopes (HA 91-108, HA 354-372, HA 307-319, NP 335-350, NP 380-393 and M2 1-18):

Serum was removed after a schedule of 3 immunizations and the specificity of Ab against the whole H3N2 influenza virus (FIG. 3A) and against the specific M2 1-18 peptide (FIG. 3B) was determined.

Binding of epitopes and stabilization of HLA-A2 on human T2 (deficient for TAP transporters and therefore express low and unstable amounts of HLA-A2.1 molecules. Upon binding of peptides, stable and high levels of HLA-A2 are expressed on the cell surface). T2 cells were incubated with various concentrations of peptides in serum-free medium over night and stained with specific monoclonal antibodies. Stabilization of HLA-A2 molecules was detected by Flow cytometry.

Figure 4:
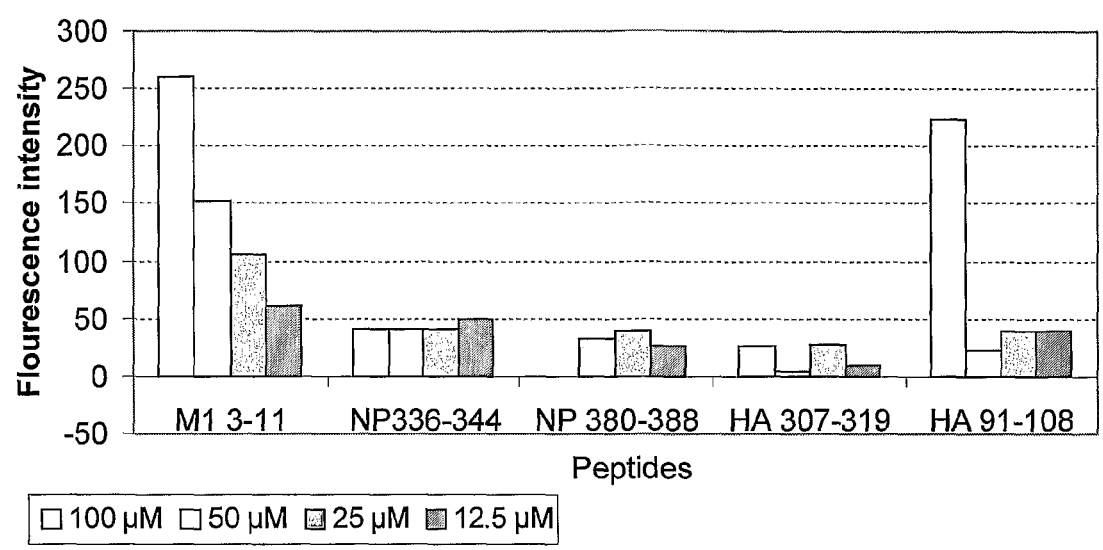

FIG. 4 shows binding of peptides to HLA-A2 on T2 cells: High and dose dependent binding was shown by the M1 3-11 peptide. Other tested peptides, NP 336-344, NP 380-388 and HA 307-319, showed some low binding capacity, which was not dose dependent. NP 380-393 is known as specific to HLA B8 molecule and is not expected to bind HLA A2. The HA 91-108 peptide which is longer than the HLA groove, showed binding capacity only at the higher (100 μM) concentration, probably due to the HLA motif in its N-terminal side. Minimal and not dose dependent binding was demonstrated at lower concentrations.

Figure 5A:
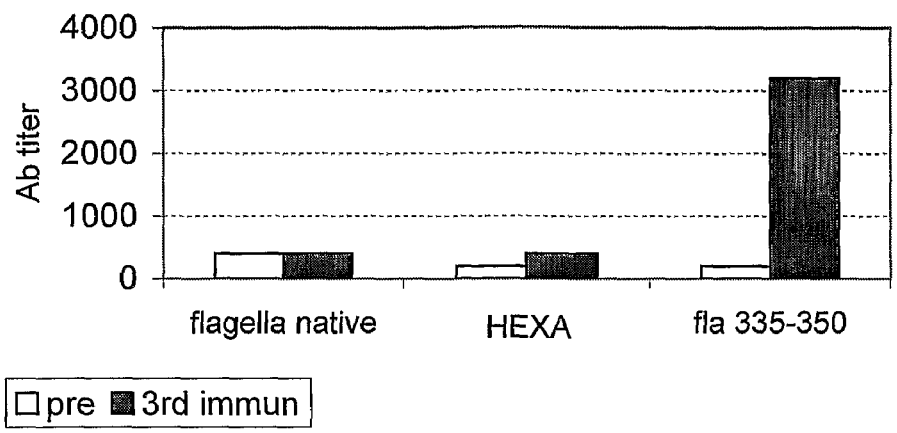
Figure 5B:
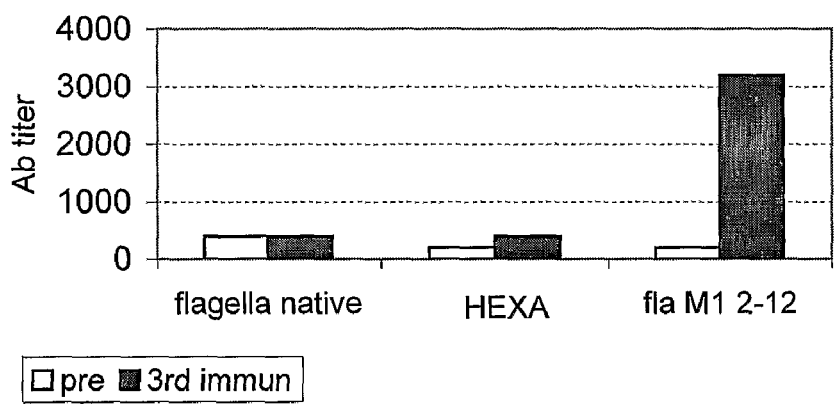
Figure 5C:
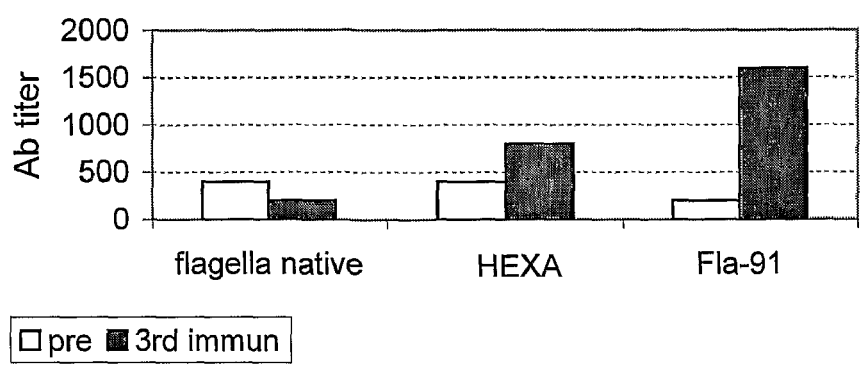

In addition to the cellular responses, sera from mice after the third immunization were compared to pre immune sera for antibodies specific to the epitopes:

FIGS. 5A-5C shows that the recombinant peptide epitopes elicit antibody protection. A significant elevation in Ab titer, specific to the epitope was obtained with epitopes NP 335-350 (5A), M1 2-12 (5B) and HA 91-108 (5C) in mice immunized with the single relevant epitope (200 μg/mouse, IM).

Conclusions

The results of this study indicate that immunization with the recombinant flagellin containing specific T cells epitopes resulted in specific recognition and cellular TH1 type response, as shown by IFN-γ secretion by lymphocytes from the vaccinated mice in response to in-vitro stimulation with the respective synthetic peptides. Furthermore, the specific binding of the investigated epitopes to HLA A2 expressing target cells as well as specific lysis of these cells loaded with the epitope by NK cells indicates cellular response to the Hexa-vaccine1 in HHD transgenic mice.

Example 9

Dose Optimization Study

This study was designed to select the optimal dose of the epitope based anti influenza vaccine Hexa-vaccine, which is the lowest effective dose conferring sufficient immune response as measured by various immunological tests. Performing this study with Hexa-vaccine assessed the efficacy of the vaccine by assessment of humoral response and virus titration in the lungs after a schedule of 3 immunizations and infection.

Study Design

HHD/HLA A2.1 mice were immunized 3 times IN and IM with 240, 80, 24 or 8 μg of Hexa-vaccine1, consisting of influenza epitopes within bacterial flagella in PBS (see Table 5 for groups and identification). Blood was collected for evaluation of the humoral response elicited in the vaccinated mice. The mice were infected with H3N2 influenza virus and viral titration in their lungs served as a correlate for efficacy.

TABLE 5

Study Groups and Identifications

| Group No. | Treatment | Route |
|---|---|---|
| A | 8 μg | IN |
| B | 24 μg | IN |
| C | 80 μg | IN |
| D | 240 μg | IN |
| E | Flagella (Control) 240 μg | IN |
| F | 8 μg | IM |
| G | 24 μg | IM |
| H | 80 μg | IM |
| I | 240 μg | IM |
| J | Flagella (Control) 240 μg | IM |

Humoral Immune Response

Figure 6:
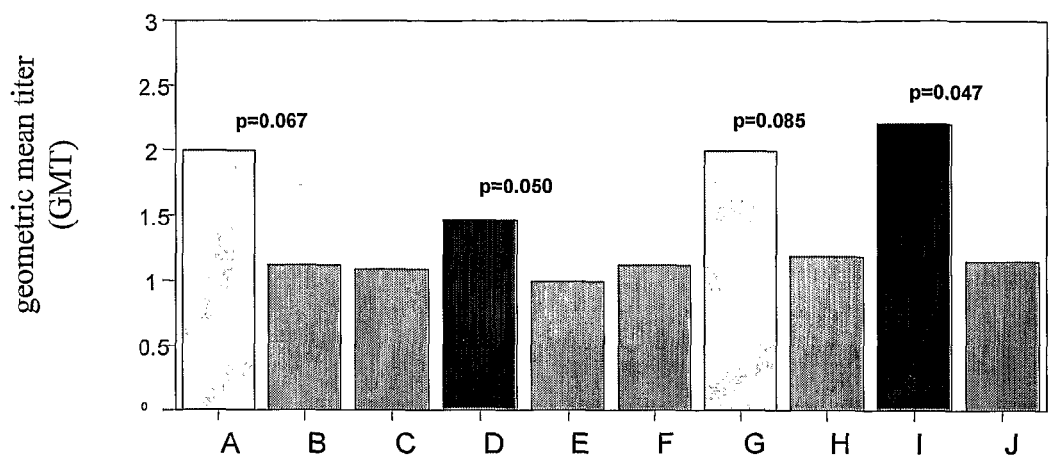
Figure 7:
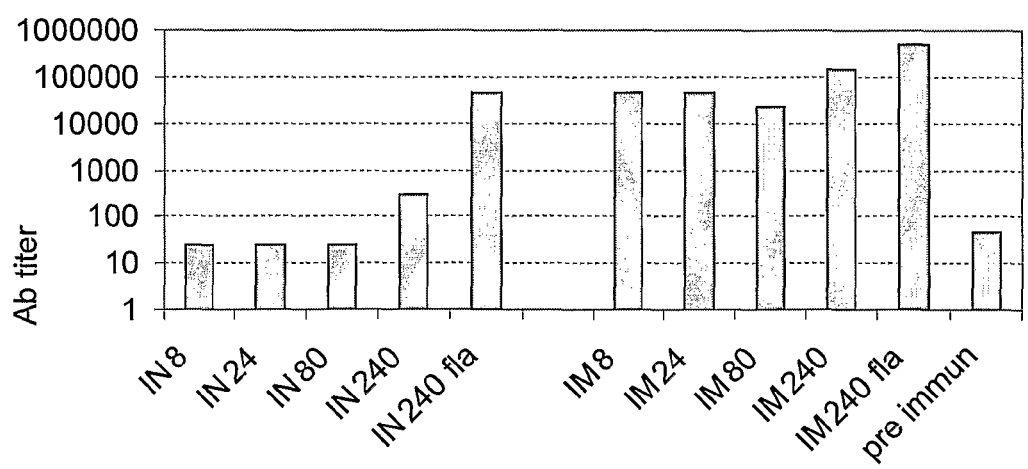
Figure 8:
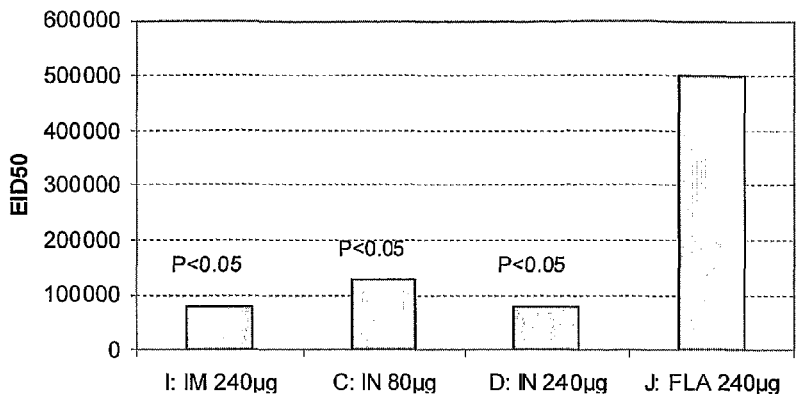
Figure 9:
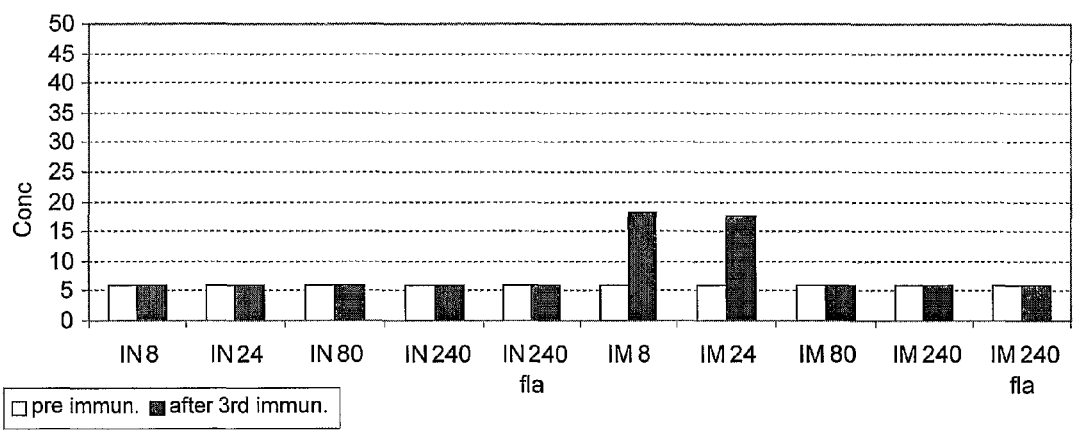

Escalating doses of Hexa-vaccine1 containing 8-240 μg of all the epitopes combined induced a specific humoral response to the H3N2 virus. The response in the groups immunized with the higher dose was significantly higher than the baseline. The change of titer between pre immune and immunized sera is shown in FIG. 6, which corresponds to the groups in Table 5. A significant elevation over the pre-immune level (p<0.05) and over the control groups E and J that were immunized with native flagella (IN or IM respectively in terms of specific recognition of influenza virus H3N2 is observed in groups D and I that were immunized with 240 μg of Hexa-vaccine1 IN or IM, respectively.

Humoral Response: Specific Recognition of Flagella

The humoral response is also directed towards the flagella carrier. The sera titer antibody to it is demonstrated in FIG. 7

FIG. 7 shows the humoral response to flagella following IN or IM administration of Hexa-vaccine1. In the IN immunized groups (left hand bars); there was an escalating dose response where the higher Ab production was found where the higher dose (IN 240 μg) was given. In the IM administrated groups (right hand bars) a similarly high response was observed in all the doses ranging from 8 μg-240 μg/mouse. By both routes, the response to the native flagella is much higher; this may result from structural changes caused by the addition of foreign epitopes that may influence its immunogenicity.

Virus Titration

After a schedule of 3 vaccinations, the mice were infected with a sub-lethal dose of influenza virus H3N2 strain (A/Texas/1/77). The lungs of the mice were removed 5 days later for titration of viral load in them. The titration was performed in fertilized eggs FIG. 8). The viral load in the groups immunized with Hexa-vaccine1 (240 μg) is comparable in both IM and IN routes and is significantly lower ($p<0.05$) than the titer in the control groups. This shows that Hexa-vaccine1 is effective and provides protection against virus infection.

Conclusions

Antibodies to (H3N2) virus: were significantly higher in the group immunized with the higher doses both IM and IN, but not in the groups immunized with lower doses, showing a dose escalating response.

Virus clearance: a lower virus titer was found in the groups immunized IN and IM, while higher viral titers were detected in animals immunized with lower doses.

These data indicates that there is a correlation between dose and response, where only the higher doses led to significant protection.

No significant weight loss, behavioral abnormalities or signs for allergy (IgE elevation) were noticed as described in the following;

Example 10

IgE Response Following Immunization

For the evaluation of potential allergic response to our product, IgE levels were measured in all major experiments conducted in mice following immunization with different combination of epitopes or with native flagella. In the various studies, mice were immunized IN or IM with the recombinant flagella, total IgE in the sera was measured by a commercial murine IgE detection kit.

Low titers of <20 ng/ml were found in immunized animals similar to the normal level in non immunized mice.

FIG. 9 presents the IgE concentration (ng/ml) in the dosing experiment and in the experiment for evaluating the cellular response. In both, IgE titers on day 0 and after the third immunization were similar.

Mice were immunized either IN or IM with Hexa-vaccine1 at escalating doses, from 8 μg-240 μg/mouse. The sera from these mice was tested for total IgE FIG. 10 represents the IgE concentration in sera of HHD transgenic (TG) mice immunized IN with recombinant flagella expressing influenza epitopes.

Conclusions

In the sera samples from mice immunized with recombinant flagella, low levels of IgE were detected. The normal range for plasma IgE is established between 19 and 200 ng/ml using wild type animals). Titers obtained in immunized animal did not exceed 20 ng/ml and therefore, Hexa-vaccine does not induce allergic responses.

Example 11

Evaluation of Hexa-Vaccine2 in Rabbits

In this study rabbits were administered IN and IM with the vaccine product in a controlled environment at a Specific Pathogen Free (SPF) certified animal house. After a schedule of 3 vaccinations, blood samples were removed and specimens from the administration site and major organs were removed and subjected to histopathological analysis.

The study groups consisted of 3 immunizations comparing Hexa-vaccine2 (6 epitopes: HA 91-108, HA 307-319, HA 354-372, NP 335-350, NP 380-393, M1 2-12) to PBS:

IN route: Hexa-vaccine2 100 µg and 50 µg/50 µl/rabbit
IM route: Hexa-vaccine2 600 µg and 300 µg/500 µl/rabbit Neither mortality nor morbidity was observed in any of the groups. Histopathology results (2 weeks post immunization) showed:

Intranasal: No toxicity in the organs examined.
Intramuscular: No toxicity in the organs examined. One animal presented focal, minimal histolytic infiltrate at injection site.

Conclusions

Figure 10:
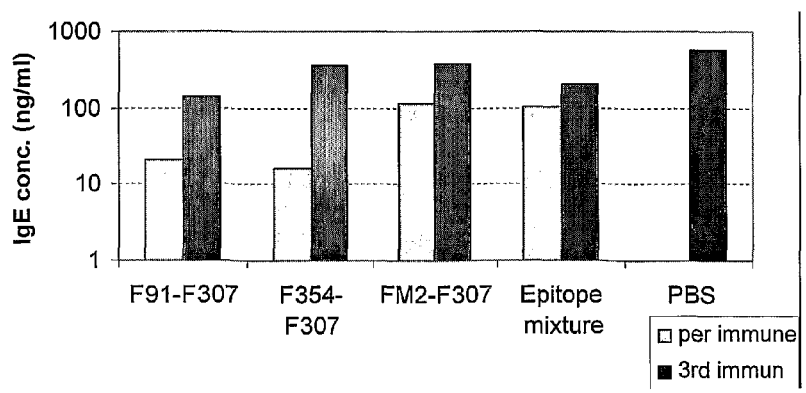
FIG. 10 shows IgE concentration (ng/ml) in sera of HHD transgenic mice immunized intranasally (IN) with recombinant flagella expressing influenza epitopes.

Safety: The Hexa-vaccine2 was found to be safe and tolerable in rabbits. Humoral response: Ab titer specific to different influenza strains was recorded in some of the rabbits. It should be noted that distinct responses were found between individual rabbits. FIG. 10 describes the fold increase in the antibody titer as compared to the pre immune titer in the responding rabbits. Non responding rabbits were excluded.

Figure 11:
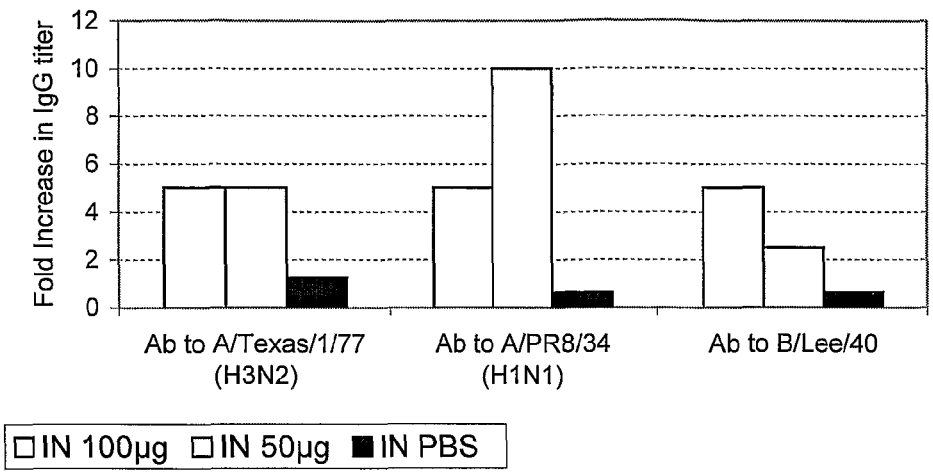
FIG. 11 shows fold increase of IgG titer to 3 different influenza strains in sera of NZW rabbits immunized intranasally three times with recombinant flagella expressing six influenza epitopes (Hexa-vaccine-2).

FIG. 11: Fold IgG titer to 3 different influenza strains in sera of NZW rabbits immunized IN 3 times with recombinant flagella expressing 6 influenza epitopes.

Example 12

Pharmacokinetics

The pharmacokinetic studies revealed that the vaccine peak in sera was obtained at 15 minutes and eliminated within 12 hours. In a parallel study with the vaccine formulated with adjuvant (Alum), the peak concentration in sera was reached after 30 minutes and the vaccine was eliminated from the sera after 24 hours (data not shown). In addition, $C_{max}$, $T_{max}$, and AUC values were calculated as described hereunder.

Study Design

The study consisted of 10 groups of 3 males and 3 females per group that were administered with a single dose of 50 µg recombinant flagella/animal. Animals were bled at 10 predetermined time points of 5, 10, 30 minutes and 1, 2, 4, 8, 12, 24 hours.

Pharmacokinetics Analysis

Calculation of the pharmacokinetic characteristics were based on the actual blood sampling time [h] (relative to the corresponding administration time of Treatment) rounded to two decimal digits and negative pre dose times set to zero. The sample before administration was used for calculation of the characteristics.

For calculation of the pharmacokinetic parameters, the following rules were applied:

Flagellin concentration values in sera at time points in the lag-time between time zero and the first quantifiable concentration were considered as zero. Evaluation of relative bioavailability was performed for the primary target parameters AUC and $C_{max}$.

The log transformed values of the primary target parameters were subject to an analysis of variance (ANOVA) model with the effects: sequence, subjects within sequence, period and treatment. The sequence effect was tested using the mean square of subjects within sequence from the ANOVA as an error term. All other effects were tested against the residual error (error mean square) from the ANOVA. Based on the ANOVA 90% confidence intervals for the treatment ratios test*100/reference [%] was calculated.

Individual treatment ratios test*100/reference [%] was given for the primary target parameters. For $T_{max}$ frequency tables were drawn by treatment based on the nominal time of the $T_{max}$ values.

FIG. 12 depicts protein serum concentration. Maximum serum concentration 3,925 ng/ml ($C_{max}$) of Hexa-vaccine was observed after 15 minutes ($T_{max}$). Half ($T_{1/2}$) of the total exposure quantity was obtained within 30 minutes post dosing. The area under the serum concentration-time curve of 15,027 ng/ml indicates the body's total exposure over time to Hexa-vaccine. No traces of protein could be detected after 12 h.

Conclusions

A typical concentration curve was obtained at the end of the pharmacokinetics study with steep rise of the curve between 5 to 15 minutes and moderate slope up until 12 hours. The maximum concentration level ($C_{max}$=3,925 ng/ml) was observed upon 15 minutes, No traces of protein in the serum could be detected upon 12 hours post dosing. The flagellin based vaccine will be totally eliminated from the sera within 12 hours.

Epitope Safety

The selected conserved epitopes utilized in the Hexa-vaccine comprise epitopes that are restricted to the most prevalent HLA molecules in human. The selected epitopes are restricted to the viral structure and are not shared by any human protein therefore they are unlikely to induce an autoimmune reaction.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

REFERENCES

Ada G L and Jones P D, "The immune response to influenza infection", Curr. Topics Microbio. Immunol. 1986; 128:1.

Anion R, Tarrab-Hazdai R, Ben-Yedidia T. Peptide-based synthetic recombinant vaccines with anti-viral efficacy. Biologicals. 2001; 29 (3-4):237-42.

Ben-Yedidia T, Marcus H, Reisner Y, Arnon R. Intranasal administration of peptide vaccine protects human/mouse radiation chimera from influenza infection. Int Immunol. 1999; 11 (7):1043-51.

Gianfrani C, Oseroff C, Sidney J, Chesnut R, Sette A. Human memory CTL response specific for influenza A virus is broad and multispecific. Hum Immunol. 2000; 61:438-452.

Ibrahim G F, Fleet G H, Lyons M J, Walker R A. Method for the isolation of highly purified *Salmonella* flagellins. J Clin Microbiol. 1985; (6):1040-4.

Jeon S H, Ben-Yedidia T, Arnon R. Intranasal immunization with synthetic recombinant vaccine containing multiple epitopes of influenza virus. Vaccine. 2002; 20 (21-22): 2772-80.

Lamb R A, Zebedee S L, Richardson C D. Influenza virus M2 protein is an integral membrane protein expressed on the infected-cell surface. Cell. 1985; 40:627-633.

Langer R. New methods of drug delivery. Science. 1990; 249 (4976):1527-33.

Liu W, Zou P, Ding J, Lu Y, Chen Y H. Sequence comparison between the extracellular domain of M2 protein human and avian influenza A virus provides new information for bivalent influenza vaccine design. Microbes Infect. 2005; 7 (2): 171-7.

Meinkoth J, Wahl G. Hybridization of nucleic acids immobilized on solid supports. Anal Biochem. 1984; 138 (2):267-84.

O'Hagan D T, Jeffery H, Davis S S. Long-term antibody responses in mice following subcutaneous immunization with ovalbumin entrapped in biodegradable microparticles. Vaccine. 1993; 11 (9):965-9.

Shapira M, Jolivet M, Arnon R. A synthetic vaccine against influenza with built-in adjuvanticity. Int J Immunopharmacol. 1985; 7:719-723.

Slepushkin V A, Katz J M, Black R A, Gamble W C, Rota P A, Cox N J. Protection of mice against influenza A virus challenge by vaccination with baculovirus-expressed M2 protein. Vaccine. 1995; 13 (15):1399-402.

Townsend A R, Skehel J J. The influenza A virus nucleoprotein gene controls the induction of both subtype specific and cross-reactive cytotoxic T cells. J Exp Med. 1984; 160 (2):552-63.

Zou P, Liu W, Chen Y H. The epitope recognized by a monoclonal antibody in influenza A virus M2 protein is immunogenic and confers immune protection. Int Immunopharmacol. 2005; 5 (4):631-5.

The invention claimed is:

1. A vaccine for immunization of a subject comprising:
   (i) two influenza virus peptide epitopes wherein the first peptide epitope is an influenza A virus matrix (M) peptide epitope selected from the group consisting of SEQ ID NOS: 25 and 26, and a second peptide epitope is a haemagglutinin (HA) peptide epitope as set forth in SEQ ID NO:48, and
   (ii) one influenza B peptide epitope of a HA 354-372 peptide as set forth in SEQ ID NO:80,
   wherein the vaccine elicits cross strain protection.

2. The vaccine according to claim 1, wherein the M peptide epitope is an M1 peptide epitope as set forth in SEQ ID NO: 26.

3. The vaccine according to claim 1, wherein:
   (i) the M peptide epitope is the M1 2-12 (SEQ ID NO:25) peptide epitope; and
   (ii) the HA peptide epitope is HA 91-108 (SEQ ID NO:48).

4. The vaccine according to claim 3, further comprising a CTL type NP peptide epitope as set forth in NP 335-350 (SEQ ID NO:67).

5. The vaccine according to claim 1, further comprising an influenza T helper (Th) type peptide epitope as set forth in HA 307-319 (SEQ ID NO:57).

6. The vaccine according to claim 1, wherein:
   (i) the M peptide epitope is an influenza A virus M peptide epitope as set forth in M1 2-12 (SEQ ID NO:25);

(ii) the HA peptide epitope is a HA 91-108 (SEQ ID NO:48) peptide epitope, with the vaccine further comprising:
(iii) a Th type peptide epitope as set forth in HA 307-319 (SEQ ID NO:57).

7. The vaccine according to claim 1, further comprising a CTL type NP peptide epitope as set forth in NP 335-350 (SEQ ID NO:67).

8. The vaccine according to claim 1, further comprising an adjuvant or an excipient.

9. The vaccine according to claim 1, wherein each of the epitopes is expressed individually within an expression vector.

10. The vaccine according to claim 9, wherein each of the epitopes is expressed individually within a recombinant flagellin.

11. The vaccine according to claim 1, wherein each of the epitopes is expressed with a polypeptide selected from the group consisting of Cholera toxin, Tetanus toxin, Ovalbumin, Tuberculosis heat shock protein, Diphtheria Toxoid, Protein G from respiratory syncytial virus, Outer Membrane Protein from *Neisseria meningitides*, nucleoprotein (N) of vesicular stomatitis virus, glycoprotein (G) of vesicular stomatitis virus, *Plasmodium falciparum* Antigen Glutamate-Rich Protein, Merozoite Surface Protein 3 or Viruses envelope (E) protein.

12. The vaccine according to claim 1, which is formulated for administration by a modality selected from the group consisting of intraperitoneal, subcutaneous, intranasal, intramuscular, oral, topical and transdermal delivery.

13. A vaccine for immunization of a subject comprises:
(i) an influenza A virus matrix (M) peptide epitope as set forth in M1 2-12 (SEQ ID NO:25);
(ii) HA 91-108 (SEQ ID NO:48);
(iii) HA 307-319 (SEQ ID NO:57);
(iv) NP 335-350 (SEQ ID NO:67); and
(v) influenza B peptide epitope HA 354-372 (SEQ ID NO:80),
wherein the vaccine elicits cross strain protection.

14. A method for eliciting an immune response and conferring protection against influenza virus in a subject, wherein the method comprises administering to the subject a vaccine according to claim 1 to elicit an immune response and confer protection against influenza virus.

15. The method according to claim 14, wherein the immune response is elicited against avian influenza, influenza A, influenza B or a combination thereof.

* * * * *